(12) United States Patent
Miller et al.

(10) Patent No.: US 7,811,764 B2
(45) Date of Patent: Oct. 12, 2010

(54) HYBRIDIZATION-BASED BIOSENSOR CONTAINING HAIRPIN PROBES AND USE THEREOF

(75) Inventors: Benjamin L. Miller, Penfield, NY (US); Christopher M. Strohsahl, Rochester, NY (US)

(73) Assignee: University of Rochester, Rochester, NY (US)

( * ) Notice: Subject to any disclaimer, the term of this patent is extended or adjusted under 35 U.S.C. 154(b) by 82 days.

(21) Appl. No.: 11/838,616

(22) Filed: Aug. 14, 2007

(65) Prior Publication Data

US 2009/0047670 A1   Feb. 19, 2009

(51) Int. Cl.
*C12Q 1/68* (2006.01)
*C07H 21/02* (2006.01)
*C07H 21/04* (2006.01)

(52) U.S. Cl. .................... 435/6; 536/23.1; 536/24.3

(58) Field of Classification Search ............... 435/6, 435/283.1; 536/22.1, 23.1, 24.3
See application file for complete search history.

(56) References Cited

U.S. PATENT DOCUMENTS

| | | | |
|---|---|---|---|
| 5,215,899 A | 6/1993 | Dattagupta | |
| 5,556,749 A | 9/1996 | Mitsuhashi et al. | |
| 6,114,121 A | 9/2000 | Fujiwara et al. | |
| 6,156,507 A * | 12/2000 | Hiramatsu et al. | 435/6 |
| 6,194,155 B1 | 2/2001 | Cohen | |
| 6,251,588 B1 | 6/2001 | Shannon et al. | |
| 6,277,607 B1 | 8/2001 | Tyagi et al. | |
| 6,312,906 B1 * | 11/2001 | Cass et al. | 435/6 |
| 6,355,421 B1 * | 3/2002 | Coull et al. | 435/6 |
| 6,355,437 B1 | 3/2002 | Neri et al. | |
| 6,365,729 B1 | 4/2002 | Tyagi et al. | |
| 6,380,377 B1 | 4/2002 | Dattagupta | |
| 6,534,284 B1 * | 3/2003 | El-Sherbeini et al. | 435/69.1 |
| 6,703,492 B1 * | 3/2004 | Kimmerly | 536/23.1 |
| 7,262,007 B2 | 8/2007 | Sauer et al. | |
| 2003/0013109 A1 | 1/2003 | Ballinger et al. | |
| 2003/0054346 A1 | 3/2003 | Shannon et al. | |
| 2003/0152971 A1 * | 8/2003 | Lyamichev et al. | 435/6 |
| 2004/0002089 A1 * | 1/2004 | Dubertret et al. | 435/6 |
| 2004/0254360 A1 * | 12/2004 | Raoult et al. | 536/23.1 |
| 2006/0160121 A1 * | 7/2006 | Mounts et al. | 435/6 |
| 2007/0059693 A1 * | 3/2007 | Miller et al. | 435/6 |
| 2007/0166731 A1 | 7/2007 | Miller et al. | |
| 2008/0008994 A1 * | 1/2008 | Stender et al. | 435/6 |

FOREIGN PATENT DOCUMENTS

| | | | |
|---|---|---|---|
| WO | WO2004/061127 | * | 7/2004 |
| WO | WO2004/061127 | * | 8/2004 |
| WO | WO2005/104813 | * | 11/2005 |

OTHER PUBLICATIONS

Archer et al., Detection of methicillin resistance in Staphylococci by using a DNA probe. Antimicrobial Agents and Chemotherapy 34(9) : 1720-1724 (1990).*
Archer et al. Dissemination among Staphylococci of DNA sequences associated with methicillin resistance. Antimicrobial Agents and Chemotherapy 38(3) : 447-454 (1994).*
Berger-Bachi et al. FemA, a host-mediated factor essential for methicillin resistance in *Staphylococcus aureus*:Molecular cloning and characterization. Molecular General Genetics 219 : 263-269 (1989).*
Du et al., Hybridization-based unquenching of DNA hairpins on Au surfaces: Prototypical "Molecular Beacon" biosensor. JACS 125:4012-4013 (2003).*
Woodford et al., Molecular Detection of Antibiotic resistance :when and where? J. of Antimicrobial Chemotherapy 56 : 259-261 (2005).*
Bonnet et al., "Thermodynamic Basis of the Enhanced Specificity of Structured DNA Probes," Proc. Natl. Acad. Sci. USA 96:6171-6176 (1999).
Dubertret et al., "Single-Mismatch Detection Using Gold-Quenched Fluorescent Oligonucleotides," Nat. Biotech. 19:365-370 (2001).
Du, et al., "Hybridization-Based Unquenching of DNA Hairpins on Au Surfaces: Prototypical "Molecular Beacon" Biosensors," J Chem Soc 125:4012-4013 (2003).
Strohsahl, Christopher M, "The Role of Secondary Structure in DNA Recognition as Applied to Pathogen Detection: Chapter 5, Towards the Detection of Antibiotic Resistance in *Staphylococcus aureus*," Ph.D. Thesis, pp. 109-136, catalogued at University of Rochester Miner Library (Nov. 9, 2006).
Piestert et al., "A Single-Molecule Sensitive DNA Hairpin System Based on Intramolecular Electron Transfer," Nano Lett. 3(7):979-982 (2003).

* cited by examiner

*Primary Examiner*—Ethan Whisenant
(74) *Attorney, Agent, or Firm*—Nixon Peabody LLP

(57) ABSTRACT

A sensor chip that includes: a fluorescence quenching surface; a nucleic acid probe that contains first and second ends with the first end bound to the fluorescence quenching surface, and is characterized by being able to self-anneal into a hairpin conformation; and a first fluorophore bound to the second end of the first nucleic acid molecule. When the first nucleic acid molecule is in the hairpin conformation, the fluorescence quenching surface substantially quenches fluorescent emissions by the first fluorophore; and when the first nucleic acid molecule is in a non-hairpin conformation, fluorescent emissions by the fluorophore are substantially free of quenching by the fluorescence quenching surface. Various nucleic acid probes, methods of making the sensor chip, biological sensor devices that contain the sensor chip, and their methods of use are also disclosed.

23 Claims, 30 Drawing Sheets

H1

(E = -7.0)

H2

(E = -4.3)

HP1

(E = -4.4)

HP1-TP1

(E = -43.2)

HP2

(E = - 4.7)

HP2-TP2

(E = - 42.6)

(E = - 10.9)

(E = - 5.6)

H3

(E = -8)

H3-T3

(E = -40.9)

H3-T3M1

(E = −34)

H3-T3

H3-T3M1

Figure 17A  Figure 17B
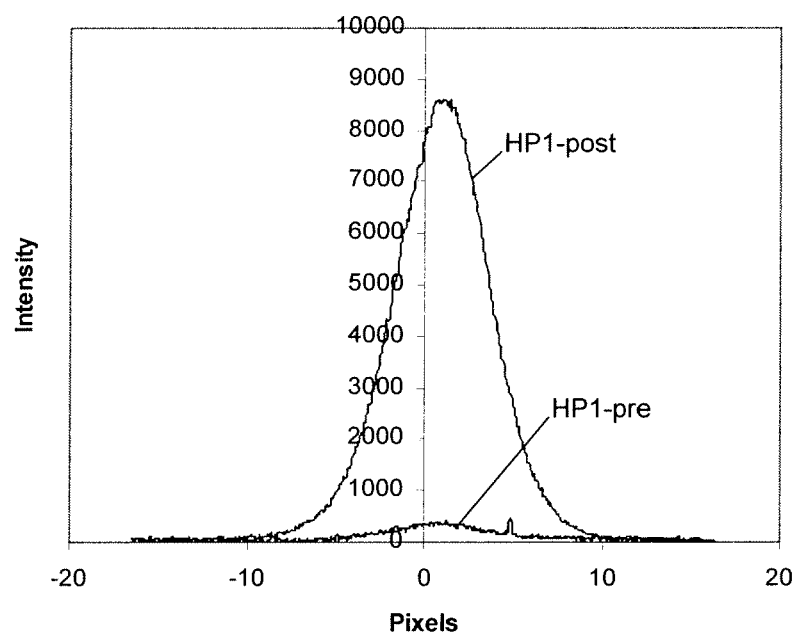
Figure 17C (E = - 4.4)

(E = - 3.8)

AH2

(E = -6.1)

BH2

(E = -3.5)

$\Delta G_{HP} = -4.2$ $\Delta G_{HP} = -3.7$ (ΔG = -3.9 kcal/mol)

(ΔG = -3.3 kcal/mol)

(ΔG = -4.4 kcal/mol)

(ΔG = -3.7 kcal/mol)

(ΔG = -9.9 kcal/mol)

(ΔG = -4.0 kcal/mol)

rpoB 147 sense
($\Delta G$ = -6.8 kcal/mol)

rpoB 147 antisense
($\Delta G$ = -8.2 kcal/mol)

rpoB 205 sense
(ΔG = -3.9 kcal/mol)

rpoB 205 antisense
(ΔG = -2.1 kcal/mol)

DnaJ 465 sense
(ΔG = -5.3 kcal/mol)

DnaJ 465 antisense
(ΔG = -2.9 kcal/mol)

DnaJ 546 sense
(ΔG = -3.3 kcal/mol)

DnaJ 546 antisense
(ΔG = -2.3 kcal/mol)

DnaJ 681 sense
(ΔG = -2.9 kcal/mol)

SEQUENCE LISTING

```
<160> NUMBER OF SEQ ID NOS: 36

<210> SEQ ID NO 1
<211> LENGTH: 48
<212> TYPE: DNA
<213> ORGANISM: Artificial
<220> FEATURE:
<223> OTHER INFORMATION: Probe

<400> SEQUENCE: 1
acacgctcat cataaccttc agcaagcttt aactcatagt gagcgtgt                48

<210> SEQ ID NO 2
<211> LENGTH: 39
<212> TYPE: DNA
<213> ORGANISM: Artificial
<220> FEATURE:
<223> OTHER INFORMATION: Probe

<400> SEQUENCE: 2
aatgatgata acccttcta cacctccata atcatcatt                          39

<210> SEQ ID NO 3
<211> LENGTH: 39
<212> TYPE: DNA
<213> ORGANISM: Artificial
<220> FEATURE:
<223> OTHER INFORMATION: Probe

<400> SEQUENCE: 3
ggtctggtcg agcgtttccg cgcgaccctc ccaaagaca                          39

<210> SEQ ID NO 4
<211> LENGTH: 39
```

<212> TYPE: DNA
<213> ORGANISM: Artificial
<220> FEATURE:
<223> OTHER INFORMATION: Probe

<400> SEQUENCE: 4
gttcggcgag cctctcttta tagcggctca acgctggac                          39

<210> SEQ ID NO 5
<211> LENGTH: 34
<212> TYPE: DNA
<213> ORGANISM: Artificial
<220> FEATURE:
<223> OTHER INFORMATION: Probe

<400> SEQUENCE: 5
tcgttagtgt taggaaaaaa tcaaacactc gcga                               34

<210> SEQ ID NO 6
<211> LENGTH: 39
<212> TYPE: DNA
<213> ORGANISM: Artificial
<220> FEATURE:
<223> OTHER INFORMATION: Probe

<400> SEQUENCE: 6
tttctttcac catggatttc taatattcat gaaaagaaa                          39

<210> SEQ ID NO 7
<211> LENGTH: 34
<212> TYPE: DNA
<213> ORGANISM: Artificial
<220> FEATURE:
<223> OTHER INFORMATION: Probe

<400> SEQUENCE: 7
tcttcaccat ggatttctaa tatccatgaa aaga                               34

<210> SEQ ID NO 8
<211> LENGTH: 31
<212> TYPE: DNA
<213> ORGANISM: Artificial
<220> FEATURE:
<223> OTHER INFORMATION: Probe

<400> SEQUENCE: 8
cgtgattcat tagttatgct aggagatcac g                                  31

<210> SEQ ID NO 9
<211> LENGTH: 33
<212> TYPE: DNA
<213> ORGANISM: Artificial
<220> FEATURE:
<223> OTHER INFORMATION: Probe

<400> SEQUENCE: 9
cgataatatg atgcctaggc agaaatatta tcg                                33

<210> SEQ ID NO 10
<211> LENGTH: 37
<212> TYPE: DNA
<213> ORGANISM: Artificial
<220> FEATURE:
<223> OTHER INFORMATION: Probe

<400> SEQUENCE: 10
tatcaataat aaacgaatag gggtgttaat attgata        37

<210> SEQ ID NO 11
<211> LENGTH: 37
<212> TYPE: DNA
<213> ORGANISM: Artificial
<220> FEATURE:
<223> OTHER INFORMATION: Complementary target molecule

<400> SEQUENCE: 11
acgctcacta tgagttaaag cttgctgaag gttatga        37

<210> SEQ ID NO 12
<211> LENGTH: 30
<212> TYPE: DNA
<213> ORGANISM: Artificial
<220> FEATURE:
<223> OTHER INFORMATION: Complementary target molecule

<400> SEQUENCE: 12
tatggaggtg tagaaggtgt tatcatcatt        30

<210> SEQ ID NO 13
<211> LENGTH: 36
<212> TYPE: DNA
<213> ORGANISM: Artificial
<220> FEATURE:
<223> OTHER INFORMATION: Probe

<400> SEQUENCE: 13
acacgctcat caagctttaa ctcatagtga gcgtgt        36

<210> SEQ ID NO 14
<211> LENGTH: 24
<212> TYPE: DNA
<213> ORGANISM: Artificial
<220> FEATURE:
<223> OTHER INFORMATION: Complementary target molecule

<400> SEQUENCE: 14
acgctcacta tgagttaaag cttg        24

<210> SEQ ID NO 15
<211> LENGTH: 24
<212> TYPE: DNA
<213> ORGANISM: Artificial
<220> FEATURE:
<223> OTHER INFORMATION: Mismatch target molecule

<400> SEQUENCE: 15
acgctgacta tgagttaaag cttg        24

<210> SEQ ID NO 16
<211> LENGTH: 39
<212> TYPE: DNA
<213> ORGANISM: Artificial
<220> FEATURE:
<223> OTHER INFORMATION: Complementary target molecule

<400> SEQUENCE: 16
tttcttttca tgaatattag aaatccatgg tgaaagaaa        39

<210> SEQ ID NO 17
<211> LENGTH: 34
<212> TYPE: DNA
<213> ORGANISM: Artificial

```
<220> FEATURE:
<223> OTHER INFORMATION: Complementary target molecule

<400> SEQUENCE: 17
tcgcgagtgt ttgattttt cctaacacta acga                                    34

<210> SEQ ID NO 18
<211> LENGTH: 33
<212> TYPE: DNA
<213> ORGANISM: Artificial
<220> FEATURE:
<223> OTHER INFORMATION: Complementary target molecule

<400> SEQUENCE: 18
cgataatatt tctgcctagg catcatatta tcg                                    33

<210> SEQ ID NO 19
<211> LENGTH: 37
<212> TYPE: DNA
<213> ORGANISM: Artificial
<220> FEATURE:
<223> OTHER INFORMATION: Complementary target molecule

<400> SEQUENCE: 19
tatcaatatt aacaccccta ttcgtttatt attgata                                37

<210> SEQ ID NO 20
<211> LENGTH: 39
<212> TYPE: DNA
<213> ORGANISM: Artificial
<220> FEATURE:
<223> OTHER INFORMATION: mecR Staphylococcus probe

<400> SEQUENCE: 20
caggttaatt tgttgaaaaa tatgaaacaa cataacatg                              39

<210> SEQ ID NO 21
<211> LENGTH: 39
<212> TYPE: DNA
<213> ORGANISM: Artificial
<220> FEATURE:
<223> OTHER INFORMATION: mecR Staphylococcus probe

<400> SEQUENCE: 21
catgttatgt tgtttcatat ttttcaacaa attaacctg                              39

<210> SEQ ID NO 22
<211> LENGTH: 31
<212> TYPE: DNA
<213> ORGANISM: Artificial
<220> FEATURE:
<223> OTHER INFORMATION: Staphylococcus aureus probe

<400> SEQUENCE: 22
gataatatga tgcctaggca gaaatattat c                                      31

<210> SEQ ID NO 23
<211> LENGTH: 31
<212> TYPE: DNA
<213> ORGANISM: Artificial
<220> FEATURE:
<223> OTHER INFORMATION: Staphylococcus aureus probe

<400> SEQUENCE: 23
gataatattt ctgcctaggc atcatattat c                                      31
```

```
<210> SEQ ID NO 24
<211> LENGTH: 39
<212> TYPE: DNA
<213> ORGANISM: Artificial
<220> FEATURE:
<223> OTHER INFORMATION: Staphylococcus aureus probe

<400> SEQUENCE: 24
atatcaataa taaacgaata ggggtgttaa tattgatat                     39

<210> SEQ ID NO 25
<211> LENGTH: 39
<212> TYPE: DNA
<213> ORGANISM: Artificial
<220> FEATURE:
<223> OTHER INFORMATION: Staphylococcus aureus probe

<400> SEQUENCE: 25
atatcaatat taacacccct attcgtttat tattgatat                     39

<210> SEQ ID NO 26
<211> LENGTH: 34
<212> TYPE: DNA
<213> ORGANISM: Artificial
<220> FEATURE:
<223> OTHER INFORMATION: Staphylococcus aureus probe

<400> SEQUENCE: 26
gtgatgtatt agaaagaaat ttataataaa tcac                          34

<210> SEQ ID NO 27
<211> LENGTH: 34
<212> TYPE: DNA
<213> ORGANISM: Artificial
<220> FEATURE:
<223> OTHER INFORMATION: Staphylococcus aureus probe

<400> SEQUENCE: 27
gtgatttatt ataaatttct ttctaataca tcac                          34

<210> SEQ ID NO 28
<211> LENGTH: 32
<212> TYPE: DNA
<213> ORGANISM: Artificial
<220> FEATURE:
<223> OTHER INFORMATION: Staphylococcus epidermidis rpoB 147 probe

<400> SEQUENCE: 28
gcagagttaa cgcacaaacg tcgtttatct gc                            32

<210> SEQ ID NO 29
<211> LENGTH: 32
<212> TYPE: DNA
<213> ORGANISM: Artificial
<220> FEATURE:
<223> OTHER INFORMATION: Staphylococcus epidermidis rpoB 147 probe

<400> SEQUENCE: 29
gcagataaac gacgtttgtg cgttaactct gc                            32

<210> SEQ ID NO 30
<211> LENGTH: 29
<212> TYPE: DNA
<213> ORGANISM: Artificial
<220> FEATURE:
<223> OTHER INFORMATION: Staphylococcus epidermidis rpoB 205 probe
```

```
<400> SEQUENCE: 30
aacgtgctca aatggaagtg cgtgacgtt                                    29

<210> SEQ ID NO 31
<211> LENGTH: 29
<212> TYPE: DNA
<213> ORGANISM: Artificial
<220> FEATURE:
<223> OTHER INFORMATION: Staphylococcus epidermidis rpoB 205 probe

<400> SEQUENCE: 31
aacgtcacgc acttccattt gagcacgtt                                    29

<210> SEQ ID NO 32
<211> LENGTH: 24
<212> TYPE: DNA
<213> ORGANISM: Artificial
<220> FEATURE:
<223> OTHER INFORMATION: Staphylococcus sciuri dnaJ 465 probe

<400> SEQUENCE: 32
cttgtacgta ctgtaacgga caag                                         24

<210> SEQ ID NO 33
<211> LENGTH: 24
<212> TYPE: DNA
<213> ORGANISM: Artificial
<220> FEATURE:
<223> OTHER INFORMATION: Staphylococcus sciuri dnaJ 465 probe

<400> SEQUENCE: 33
cttgtccgtt acagtacgta caag                                         24

<210> SEQ ID NO 34
<211> LENGTH: 24
<212> TYPE: DNA
<213> ORGANISM: Artificial
<220> FEATURE:
<223> OTHER INFORMATION: Staphylococcus sciuri dnaJ 546 probe

<400> SEQUENCE: 34
gtcctgaatg tgaaggttct ggac                                         24

<210> SEQ ID NO 35
<211> LENGTH: 24
<212> TYPE: DNA
<213> ORGANISM: Artificial
<220> FEATURE:
<223> OTHER INFORMATION: Staphylococcus sciuri dnaJ 546 probe

<400> SEQUENCE: 35
gtccagaacc ttcacattca ggac                                         24

<210> SEQ ID NO 36
<211> LENGTH: 24
<212> TYPE: DNA
<213> ORGANISM: Artificial
<220> FEATURE:
<223> OTHER INFORMATION: Staphylococcus sciuri dnaJ 681 probe

<400> SEQUENCE: 36
tagctggtaa aggtggtcca ggta                                         24
```

HYBRIDIZATION-BASED BIOSENSOR CONTAINING HAIRPIN PROBES AND USE THEREOF

The present invention was made in part with funding by the Department of Energy under grant DE-FG-02-02ER63410.A000. The U.S. government has certain rights in this invention.

FIELD OF THE INVENTION

The present invention relates to hybridization-based biosensors containing hairpin probes and their use in identifying target nucleic acids in samples.

BACKGROUND OF THE INVENTION

Recent intense interest in the use of rapid genetic analysis as a tool for understanding biological processes (Wodicka et al., *J. Nat. Biotechnol.* 15:1359-1367 (1997); Iyer et al., *Science* 283:83-87 (1999)), in unlocking the underlying molecular causes of disease, and in the development of biosensors, has led to a need for new sensitive and arrayable chip-based analytical tools. Of high importance is the need for techniques that do not require labeling of the target sample (Sando et al., *J. Am. Chem. Soc.* 124:2096-2097 (2002), since that increases the time, cost, and potential for error inherent in the analysis. In the context of solution-phase assays, the molecular beacon concept has proven itself to be both sensitive and reliable (Broude, *Trends Biotech.* 20:249-256 (2002); Dubertret et al., *Nature Biotech.* 19:365-370 (2001)). Molecular beacons consist of a DNA hairpin functionalized at one end with a fluorophore, and at the other with a quenching agent (Tyagi et al., *Nat Biotechnol* 14:303-308 (1996); Joshi et al., *Chem. Commun.* 1(6):549-550 (2001)). In the absence of the target DNA sequence, the quencher is brought in close proximity to the fluorophore, and no signal is generated. Addition of the target sequence leads to hairpin unfolding, concomitant duplex formation, and signal generation.

Although a few reports of surface-immobilized molecular beacons have appeared in the literature (Fang et al., *J. Am. Chem. Soc.* 121:2921-2922 (1999); Wang et al., *Nucl. Acids. Res.* 30:e61 (2002)), it is believed that these approaches employ an attached single molecule as quencher, while the material on (or in) which the hairpin is immobilized serves only a passive role. As part of a general program aimed at developing "label-free" optical biosensors (Chan et al., *J. Am. Chem. Soc.* 123:11797-11798 (2001)), it was of interest, therefore, to investigate whether the substrate material itself could be used as a quenching agent.

When attempting to adapt the work of Dubertret et al. (*Nature Biotech.* 19:365-370 (2001)) by attaching fluorophore-functionalized DNA hairpins to a flat gold surface rather than a gold nanoparticle, as described by Dubertret et al., the inventors of the present application obtained a device that was not functional, presumably because of steric crowding. The gold nanoparticles used by Dubertret et al. contained only a single hairpin per particle; whereas multiple hairpins were bonded to the flat gold surface.

The present invention is directed to overcoming these and other deficiencies in the art.

SUMMARY OF THE INVENTION

A first aspect of the present invention relates to a sensor chip that includes: a fluorescence quenching surface; a first nucleic acid molecule (i.e., as a probe) that contains first and second ends with the first end bound to the fluorescence quenching surface, a first region, and a second region complementary to the first region, the first nucleic acid molecule having, under appropriate conditions, either a hairpin conformation with the first and second regions hybridized together or a non-hairpin conformation; and a first fluorophore bound to the second end of the first nucleic acid molecule. When the first nucleic acid molecule is in the hairpin conformation, the fluorescence quenching surface substantially quenches fluorescent emissions by the first fluorophore; and when the first nucleic acid molecule is in the non-hairpin conformation (i.e., in the presence of a target nucleic acid molecule), fluorescent emissions by the fluorophore are substantially free of quenching by the fluorescence quenching surface.

A second aspect of the present invention relates to a biological sensor device that contains a sensor chip according to the first aspect of the present invention, a light source that illuminates the sensor chip at a wavelength suitable to induce fluorescent emissions by the first fluorophore, and a detector positioned to detect fluorescent emissions by the first fluorophore.

A third aspect of the present invention relates to nucleic acid molecules that can be used as probes on sensor chips in accordance with the first aspect of the present invention. The nucleic acid probe includes first and second ends, the first end being modified for coupling to a surface and the second end being bound to a fluorophore, the nucleic acid probe further including a first region, and a second region complementary to the first region, wherein, under appropriate conditions, the nucleic acid probe has either a hairpin conformation with the first and second regions hybridized together or a non-hairpin conformation, with one or both of the first and second regions being adapted for hybridization to a target nucleic acid molecule.

A fourth aspect of the present invention relates to a method of detecting the presence of a target nucleic acid molecule in a sample. This method of the invention is carried out by: exposing the sensor chip according to the first aspect of the present invention to a sample under conditions effective to allow any target nucleic acid molecule in the sample to hybridize to at least a portion of the first and/or second regions of the first nucleic acid molecule; illuminating the sensor chip with light sufficient to cause emission of fluorescence by the first fluorophore; and determining whether or not the sensor chip emits fluorescent emission of the first fluorophore upon said illuminating, wherein fluorescent emission by the sensor chip indicates that the first nucleic acid molecule is in the non-hairpin conformation and therefore that the target nucleic acid molecule is present in the sample.

A fifth aspect of the present invention relates to a method of genetic screening that is carried out by performing the method according to the fourth aspect of the present invention using a sensor chip having a first nucleic acid molecule with the first and/or second region thereof specific for hybridization with a first genetic marker.

A sixth aspect of the present invention relates to a method of detecting the presence of a pathogen in a sample that includes performing the method according to the fourth aspect of the present invention with a sensor chip having a first nucleic acid molecule with at least a portion of the first and/or second region thereof specific for hybridization with a target nucleic acid molecule of a pathogen.

A seventh aspect of the present invention relates to a method of making a sensor chip of the present invention. This method is carried out by: providing a fluorescence quenching surface; exposing the fluorescence quenching surface to a plurality of first nucleic acid molecules each comprising first and second ends with the first end being modified for coupling to the fluorescence quenching surface, a first region, and a second region complementary to the first region, and each first nucleic acid molecule having, under appropriate conditions, either a hairpin conformation with the first and second regions hybridized together or a non-hairpin conformation; and exposing the fluorescence quenching surface to a plurality of spacer molecules each including a reactive group capable of coupling to the fluorescence quenching surface, whereby the plurality of spacer molecules, when bound to the fluorescence quenching surface, inhibit interaction between adjacent first nucleic acid molecules bound to the fluorescence quenching surface (i.e., thereby minimizing background fluorescence by the sensor chip in the absence of target nucleic acid molecules).

An eighth aspect of the present invention relates to an isolated nucleic acid molecule that is less than about 60 nucleotides in length, is characterized by being able to self-anneal into a hairpin configuration, and hybridizes over substantially the entire length thereof to nucleic acids from methicillin-resistant *Staphylococcus* spp. Preferred nucleic acid molecules include the nucleotide sequence of SEQ ID NO: 20 or SEQ ID NO: 21.

The present invention allows for the simple construction of single or arrayed sensors in a convenient format. In particular, the use of secondary sensor agents is obviated by the presence of the quenching agent and the fluorescent agent in a single structural arrangement. Following one or more hybridization procedures, presence or absence of target nucleic acids is identified by the presence of a fluorescent signal emitted by a fluorophore bound to the hairpin probe that is tethered to the quenching substrate. The sensor chips and sensing devices of the present invention allow for a visual inspection by a person or instrument to see one or more colors, allowing for the simple detection of even low levels of target nucleic acids. These results could not be achieved with the molecular beacons employed, for example, by Dubertret et al. (*Nature Biotech.* 19:365-370 (2001), which is hereby incorporated by reference in its entirety). Moreover, the methods and devices of the present invention can also take advantage of surface enhancement of the electric field caused by the fluorescence quenching surface to attain orders of magnitude more signal per photon than that achieved by Dubertret et al.

BRIEF DESCRIPTION OF THE DRAWINGS

FIGS. 14A-C are digital images showing post-immobilization of sequence H1 (14A), post treatment with 1.38 μM of hybridizing target sequence T1 (14B), and post treatment with 1.38 μM salmon sperm DNA (14C). FIG. 14D is a graph illustrating the following binned CCD intensity images: curves (a) and (d) show fluorescence pre-immobilization of sequence H1, curves (b) and (e) show fluorescence post-immobilization of sequence H1, curve (c) shows fluorescence post treatment with 1.38 μM of hybridizing target sequence T1, and curve (f) shows post treatment with 1.38 μM salmon sperm DNA.

FIGS. 17A-C illustrate the hybridization-dependent fluorescence efficiency of a sensor chip containing hairpin probe HP1. FIG. 17A-B are digital images showing post-immobilization of hairpin probe HP1 (17A), and post treatment with 1.3 μM of hybridizing target sequence TP1 (17B). The graph presented in FIG. 17C represents the binned CCD images, which illustrate a nearly 24-fold increase in fluorescence intensity upon target binding.

FIG. 18A-B are digital images showing post-immobilization of hairpin probe HP2 (18A), and post treatment with 2.6 μM of hybridizing target sequence TP2 (18B). The graph presented in FIG. 18C represents the binned CCD images, which illustrate a nearly six-fold increase in fluorescence intensity upon target binding.

FIG. 19A is a CCD image of chip AB-3 with two probes before hybridization, and FIG. 19B is a CCD image of the same chip after hybridization with AH2C. FIG. 19C is a CCD image of chip AB-4 with two probes before hybridization, and FIG. 19D is a CCD image of chip AB-4 with two probes after hybridization with BH2C.

FIG. 20A illustrates the fluorescence spectra of probe AH2-Rhodamine on chip AB-3 before and after hybridization with AH2C. FIG. 20B illustrates the fluorescence spectra of probe BH2-Cy5 on chip AB-3 before and after hybridization with AH2C. FIG. 20C illustrates the binning results of CCD images from FIGS. 19A-B. For chip AB-3, the increase of Rhodamine is higher than that of Cy5, so the fluorescence increase of the chip is mainly due to probe AH2-AH2C hybridization, rather than BH2-AH2C hybridization. The increase in fluorescence emission for chip AB-3 is about 3.6-fold. FIG. 20D illustrates the fluorescence spectra of probe AH2-Rhodamine on chip AB-4 before and after hybridization with BH2C. FIG. 20E illustrates the fluorescence spectra of probe BH2-Cy5 on chip AB-4 before and after hybridization with BH2C. FIG. 20F illustrates the binning results of CCD images from FIGS. 19C-D. For chip AB-4, the increase of Cy5 is higher than that of Rhodamine, so the fluorescence increase of the chip is mainly due to probe BH2-BH2C hybridization, rather than AH2-BH2C hybridization. The increase in fluorescence emission for chip AB-4 is about 1.6-fold.

entirety) and RNAStructure version 4.2 (Mathews et al., *Proc. Natl. Acad. Sci.* 101:7287-7792 (2004), which is hereby incorporated by reference in its entirety).

Figure 25:
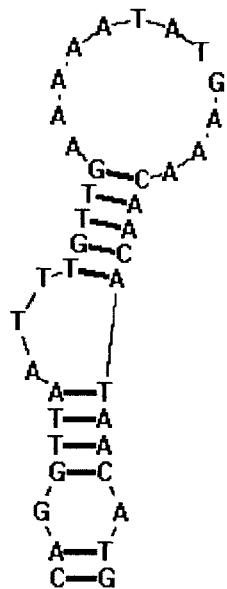
Figure 27:
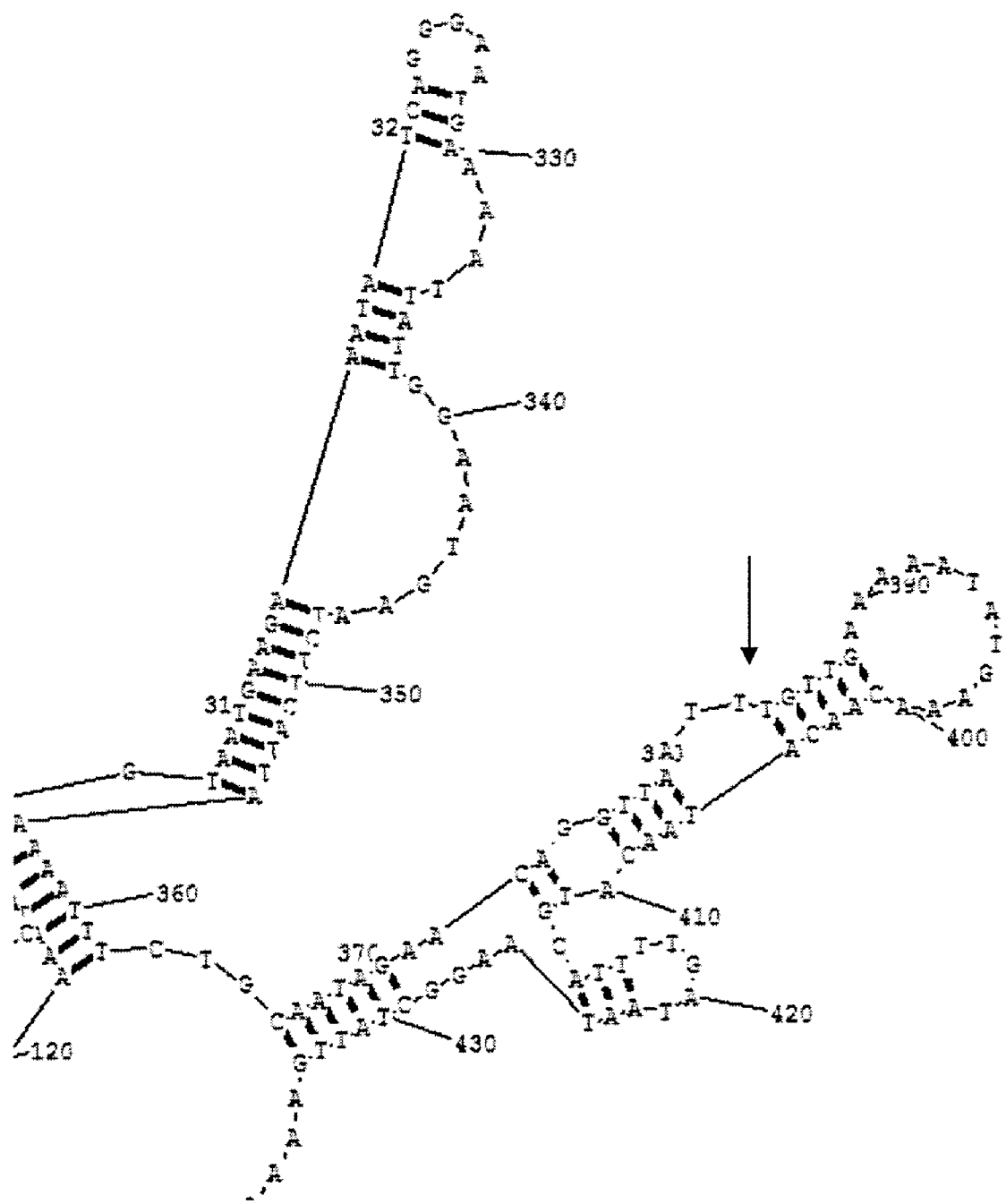

FIG. 27 illustrates a portion of the secondary structure analysis of the *Staphylococcus aureus* mecR gene as predicted by RNAStructure version 3.7. The arrow identifies the natural hairpin of the target that was used to design the hairpin probe of SEQ ID NO: 20 (FIG. 25).

Figure 28:
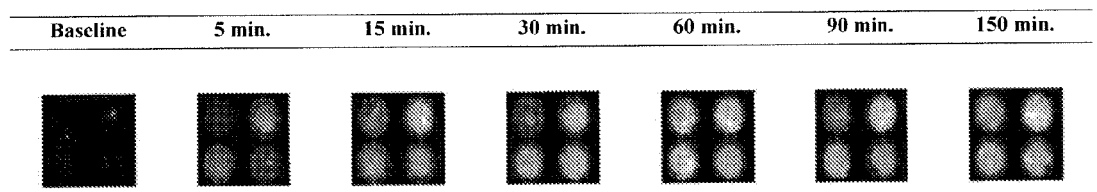

FIG. 28 is an image showing the time course response to the introduction of target DNA to the surface immobilized probe. Target solution contained 2.5 µM synthetic target DNA in 0.5 M NaCl, 20 mM cacodylic acid, and 0.5 mM EDTA. Hybridization was performed at 22° C.

Figure 29:
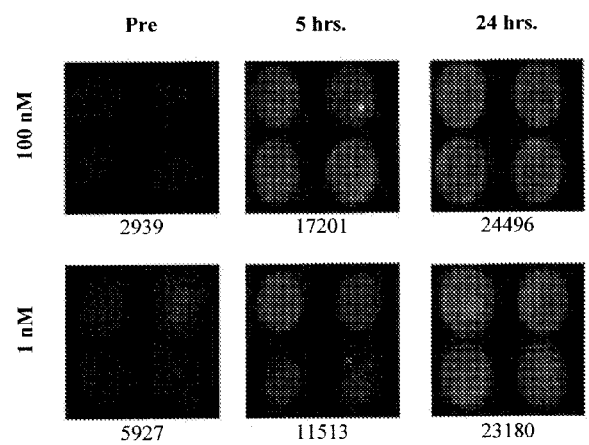

FIG. 29 shows the detection of synthetic target for the mecR probe in mixed media. Both target solutions contained 230 µg/mL of total RNA purified from a 100 mL culture of MRSA. The solutions were also spiked with synthetic target DNA in the concentrations indicated. The DNA was diluted in 0.5 M NaCl, 20 mM cacodylic acid, and 0.5 mM EDTA. Hybridization was performed at 22° C.

Figure 30:
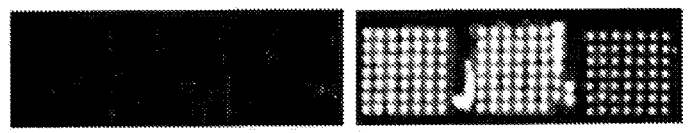

FIG. 30 shows images of the 200×600 µm area containing a 2 µM mecR/10 µM mercaptopropanol solution arrayed onto a gold surface taken before and after treatment with a 2.5 µM target solution.

Figure 31:
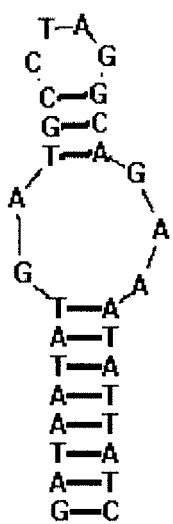

FIG. 31 illustrates the secondary structure of a hairpin (SEQ ID NO: 22) targeted to the *Staphylococcus aureus* genome (ORFID SA4_9). The folding structure was predicted using RNAStructure version 3.7 (Mathews et al., *J. Mol. Biol.* 289:911-940 (1999), which is hereby incorporated by reference in its entirety) and RNAStructure version 4.2 (Mathews et al., *Proc. Natl. Acad. Sci.* 101:7287-7792 (2004), which is hereby incorporated by reference in its entirety).

Figure 32:
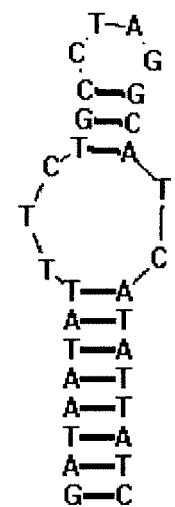

FIG. 32 illustrates the secondary structure of a hairpin (SEQ ID NO: 23) complementary to SEQ ID NO: 22 and also targeted to the *Staphylococcus aureus* genome (ORFID SA4_9B). The folding structure was predicted using RNAStructure version 3.7 (Mathews et al., *J. Mol. Biol.* 289:911-940 (1999), which is hereby incorporated by reference in its entirety) and RNAStructure version 4.2 (Mathews et al., *Proc. Natl. Acad. Sci.* 101:7287-7792 (2004), which is hereby incorporated by reference in its entirety).

Figure 33:
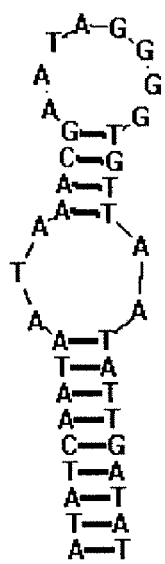

FIG. 33 illustrates the secondary structure of a hairpin (SEQ ID NO: 24) targeted to the *Staphylococcus aureus* genome (ORFID SA4_7_BH). The folding structure was predicted using RNAStructure version 3.7 (Mathews et al., *J. Mol. Biol.* 289:911-940 (1999), which is hereby incorporated by reference in its entirety) and RNAStructure version 4.2 (Mathews et al., *Proc. Natl. Acad. Sci.* 101:7287-7792 (2004), which is hereby incorporated by reference in its entirety).

Figure 34:
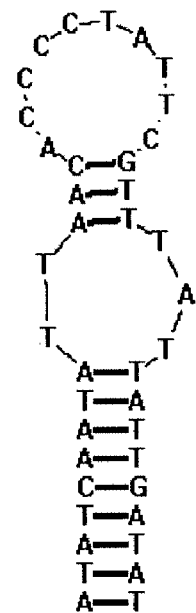

FIG. 34 illustrates the secondary structure of a hairpin (SEQ ID NO: 25) complementary to SEQ ID NO: 24 and also targeted to the *Staphylococcus aureus* genome (ORFID SA4_7_BHB). The folding structure was predicted using RNAStructure version 3.7 (Mathews et al., *J. Mol. Biol.* 289:911-940 (1999), which is hereby incorporated by reference in its entirety) and RNAStructure version 4.2 (Mathews et al., *Proc. Natl. Acad. Sci.* 101:7287-7792 (2004), which is hereby incorporated by reference in its entirety).

Figure 35:
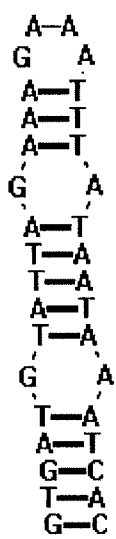

FIG. 35 illustrates the secondary structure of a hairpin (SEQ ID NO: 26) targeted to the *Staphylococcus aureus* genome (ORFID SA4_15). The folding structure was predicted using RNAStructure version 3.7 (Mathews et al., *J. Mol. Biol.* 289:911-940 (1999), which is hereby incorporated by reference in its entirety) and RNAStructure version 4.2 (Mathews et al., *Proc. Natl. Acad. Sci.* 101:7287-7792 (2004), which is hereby incorporated by reference in its entirety).

Figure 36:

FIG. 36 illustrates the secondary structure of a hairpin (SEQ ID NO: 27) complementary to SEQ ID NO: 26 and also targeted to the *Staphylococcus aureus* genome (ORFID SA4_15B). The folding structure was predicted using RNAStructure version 3.7 (Mathews et al., *J. Mol. Biol.* 289:911-940 (1999), which is hereby incorporated by reference in its entirety) and RNAStructure version 4.2 (Mathews et al., *Proc. Natl. Acad. Sci.* 101:7287-7792 (2004), which is hereby incorporated by reference in its entirety).

Figure 37:
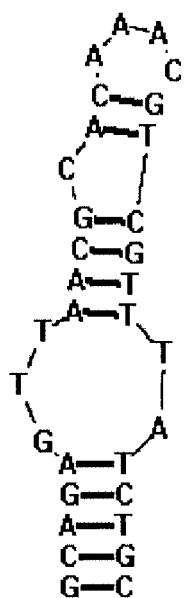

FIG. 37 illustrates the secondary structure of a hairpin (SEQ ID NO: 28) targeted to a portion (nt 147-178) of the *Staphylococcus epidermidis* RNA polymerase B (rpoB) gene. This probe is designated "rpoB 147 sense." The folding structure was predicted using RNAStructure version 3.7 (Mathews et al., *J. Mol. Biol.* 289:911-940 (1999), which is hereby incorporated by reference in its entirety) and RNAStructure version 4.2 (Mathews et al., *Proc. Natl. Acad. Sci.* 101:7287-7792 (2004), which is hereby incorporated by reference in its entirety).

Figure 38:
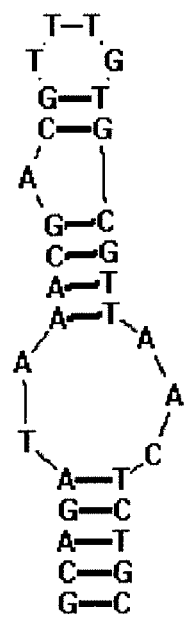

FIG. 38 illustrates the secondary structure of a hairpin (SEQ ID NO: 29) complementary to SEQ ID NO: 29 and targeted to the same portion of the *Staphylococcus epidermidis* rpoB gene. This probe is designated "rpoB 147 antisense." The folding structure was predicted using RNAStructure version 3.7 (Mathews et al., *J. Mol. Biol.* 289:911-940 (1999), which is hereby incorporated by reference in its entirety) and RNAStructure version 4.2 (Mathews et al., *Proc. Natl. Acad. Sci.* 101:7287-7792 (2004), which is hereby incorporated by reference in its entirety).

Figure 39:
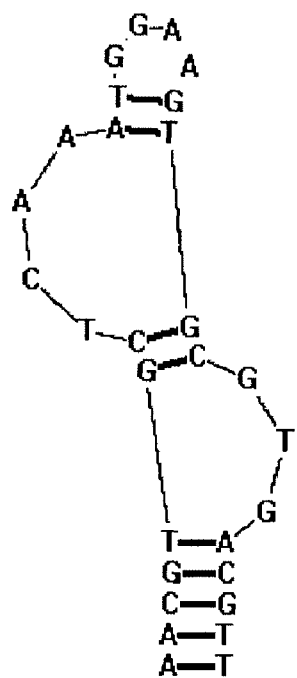

FIG. 39 illustrates the secondary structure of a hairpin (SEQ ID NO: 30) targeted to a portion (nt 205-233) of the *Staphylococcus epidermidis* rpoB gene. This probe is designated "rpoB 205 sense." The folding structure was predicted using RNAStructure version 3.7 (Mathews et al., *J. Mol. Biol.* 289:911-940 (1999), which is hereby incorporated by reference in its entirety) and RNAStructure version 4.2 (Mathews et al., *Proc. Natl. Acad. Sci.* 101:7287-7792 (2004), which is hereby incorporated by reference in its entirety).

Figure 40:
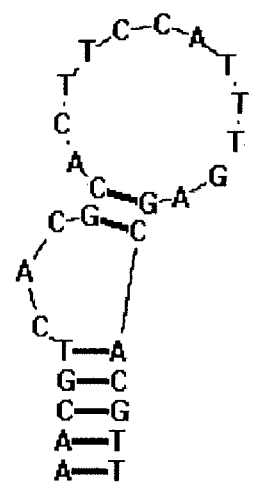

FIG. 40 illustrates the secondary structure of a hairpin (SEQ ID NO: 31) complementary to SEQ ID NO: 30 and targeted to the same portion of the *Staphylococcus epidermidis* rpoB gene. This probe is designated "rpoB 205 antisense." The folding structure was predicted using RNAStructure version 3.7 (Mathews et al., *J. Mol. Biol.* 289:911-940 (1999), which is hereby incorporated by reference in its entirety) and RNAStructure version 4.2 (Mathews et al., *Proc. Natl. Acad. Sci.* 101:7287-7792 (2004), which is hereby incorporated by reference in its entirety).

Figure 41:
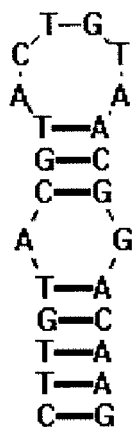

FIG. 41 illustrates the secondary structure of a hairpin (SEQ ID NO: 32) targeted to a portion (nt 465-488) of the *Staphylococcus sciuri* dnaJ gene. This probe is designated "dnaJ 465 sense." The folding structure was predicted using RNAStructure version 3.7 (Mathews et al., *J. Mol. Biol.* 289:911-940 (1999), which is hereby incorporated by reference in its entirety) and RNAStructure version 4.2 (Mathews et al., *Proc. Natl. Acad. Sci.* 101:7287-7792 (2004), which is hereby incorporated by reference in its entirety).

Figure 42:
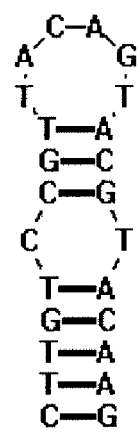

FIG. 42 illustrates the secondary structure of a hairpin (SEQ ID NO: 33) complementary to SEQ ID NO: 32 and targeted to the same portion of the *Staphylococcus sciuri* dnaJ gene. This probe is designated "dnaJ 465 antisense." The folding structure was predicted using RNAStructure version 3.7 (Mathews et al., *J. Mol. Biol.* 289:911-940 (1999), which is hereby incorporated by reference in its entirety) and RNA- Structure version 4.2 (Mathews et al., *Proc. Natl. Acad. Sci.* 101:7287-7792 (2004), which is hereby incorporated by reference in its entirety).

Figure 43:
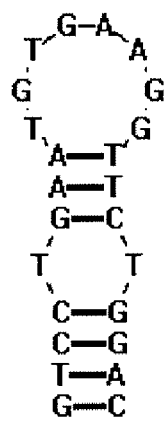

FIG. 43 illustrates the secondary structure of a hairpin (SEQ ID NO: 34) targeted to a portion (nt 546-569) of the *Staphylococcus sciuri* dnaJ gene. This probe is designated "dnaJ 546 sense." The folding structure was predicted using RNAStructure version 3.7 (Mathews et al., *J. Mol. Biol.* 289: 911-940 (1999), which is hereby incorporated by reference in its entirety) and RNAStructure version 4.2 (Mathews et al., *Proc. Natl. Acad. Sci.* 101:7287-7792 (2004), which is hereby incorporated by reference in its entirety).

Figure 44:
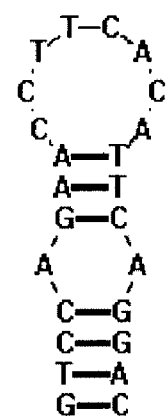

FIG. 44 illustrates the secondary structure of a hairpin (SEQ ID NO: 35) complementary to SEQ ID NO: 34 and targeted to the same portion of the *Staphylococcus sciuri* dnaJ gene. This probe is designated "dnaJ 546 antisense." The folding structure was predicted using RNAStructure version 3.7 (Mathews et al., *J. Mol. Biol.* 289:911-940 (1999), which is hereby incorporated by reference in its entirety) and RNA-Structure version 4.2 (Mathews et al., *Proc. Natl. Acad. Sci.* 101:7287-7792 (2004), which is hereby incorporated by reference in its entirety).

Figure 45:
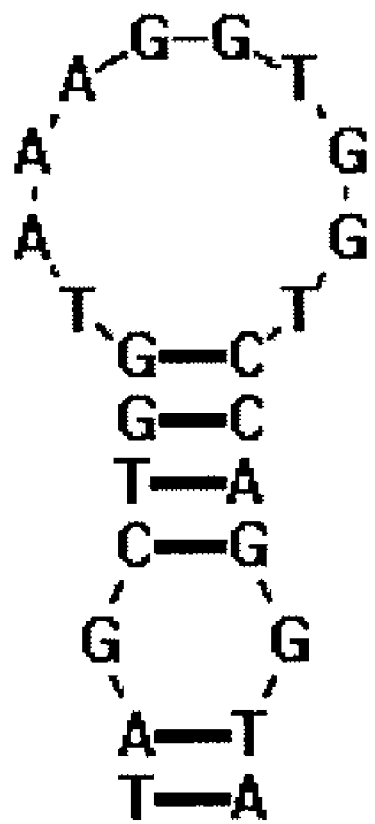

FIG. 45 illustrates the secondary structure of a hairpin (SEQ ID NO: 36) targeted to a portion (nt 681-704) of the *Staphylococcus sciuri* dnaJ gene. This probe is designated "dnaJ 681 sense." The folding structure was predicted using RNAStructure version 3.7 (Mathews et al., *J. Mol. Biol.* 289: 911-940 (1999), which is hereby incorporated by reference in its entirety) and RNAStructure version 4.2 (Mathews et al., *Proc. Natl. Acad. Sci.* 101:7287-7792 (2004), which is hereby incorporated by reference in its entirety).

DETAILED DESCRIPTION OF THE INVENTION

Figure 1:
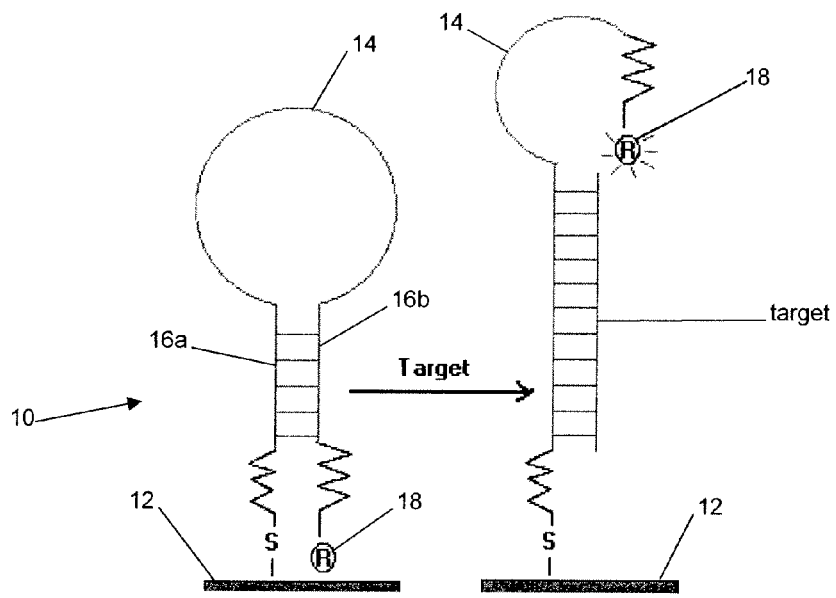
FIG. 1 illustrates a sensor chip of the present invention. A hairpin nucleic acid molecule is immobilized at one end thereof to a fluorescent quenching surface, and the other end thereof has attached thereto a fluorophore. In the hairpin conformation, the fluorophore is in sufficiently close proximity to the fluorescent quenching surface such that fluorescent emissions of the fluorophore are quenched. In the presence of a target nucleic acid molecule, the hairpin conformation is lost, resulting in fluorescent emissions that are no longer quenched by the fluorescent quenching surface.

One aspect of the present invention relates to a sensor chip that can be used to detect the presence of target nucleic acid molecules in a sample. As shown in FIG. 1, the sensor chip 10 includes: a fluorescence quenching surface 12; one or more nucleic acid molecules 14 (i.e., as probes) each having first and second ends with the first end bound to the fluorescence quenching surface, a first region 16a, and a second region 16b complementary to the first region; and a first fluorophore 18 bound to the second end of the nucleic acid molecule 14.

Suitable nucleic acid probes can be DNA, RNA, or PNA. The nucleic acid probes of the present invention can also possess one or more modified bases, one or more modified sugars, one or more modified backbones, or combinations thereof. The modified bases, sugars, or backbones can be used either to enhance the affinity of the probe to a target nucleic acid molecule or to allow for binding to the fluorescence quenching surface as described hereinafter. Exemplary forms of modified bases are known in the art and include, without limitation, alkylated bases, alkynylated bases, thiouridine, and G-clamp (Flanagan et al., *Proc. Natl. Acad. Sci. USA* 30:3513-3518 (1999), which is hereby incorporated by reference in its entirety). Exemplary forms of modified sugars are known in the art and include, without limitation, LNA, 2'-O-methyl, 2'-O-methoxyethyl, and 2'-fluoro (see, e.g., Freier and Attmann, *Nucl. Acids Res.* 25:4429-4443 (1997), which is hereby incorporated by reference in its entirety). Exemplary forms of modified backbones are known in the art and include, without limitation, phosphoramidates, thiophosphoramidates, and alkylphosphonates. Other modified bases, sugars, and/or backbones can, of course, be utilized.

With the first and second regions 16a,16b of the nucleic acid probes 14 being complementary to one another, the nucleic acid probes have, under appropriate conditions, either (i) a hairpin conformation with the first and second regions hybridized together (shown on the left side of FIG. 1) or (ii) a non-hairpin conformation (shown on the right side of FIG. 1). The conditions under which the hairpin conformation exists is when the nucleic acid probe is maintained below its melting temperature (i.e., considering the length of the first and second regions, the GC content of those regions, and salt concentration), and typically when the target nucleic acid is not present. The conditions under which the non-hairpin conformation exists is either when the first nucleic acid is maintained above its melting temperature and/or when the probe is hybridized to its target nucleic acid (as shown in FIG. 1).

The overall length of the nucleic acid probe is preferably between about 12 and about 60 nucleotides, more preferably between about 20 and about 50 nucleotides, most preferably between about 30 and about 40 nucleotides. It should be appreciated, however, that longer or shorter nucleic acids can certainly be used. The first and second regions of the nucleic acid probes are preferably at least about 4 nucleotides in length, more preferably at least about 5 nucleotides in length or at least about 6 nucleotides in length. In the preferred embodiments described above, the first and second regions can be up to about 28 nucleotides in length, depending on the overall length of the nucleic acid probe and the size of a loop region present between the first and second regions. It is believed that a loop region of at least about 4 or 5 nucleotides is needed to allow the hairpin to form. The first and second regions can be perfectly matched (i.e., having 100 percent complementary sequences that form a perfect stem structure of the hairpin conformation) or less than perfectly matched (i.e., having non-complementary portions that form bulges within a non-perfect stem structure of the hairpin conformation). When the first and second regions are not perfectly matched the first and second regions can be the same length or they can be different in length, although they should still have at least 4 complementary nucleotides.

Nucleic acid probes of the present invention can have their entire length or any portion thereof targeted to hybridize to the target nucleic acid molecule, which can be RNA or DNA. Thus, the entire probe can hybridize to a target sequence of the target nucleic acid molecule or, alternatively, a portion thereof can hybridize to a target sequence of the target nucleic acid molecule. When less than the entire nucleic acid probe is intended to hybridize to the target nucleic acid molecule, the portion thereof that does hybridize (to the target nucleic acid molecule) should be at least about 50 percent, preferably at least about 60 or 70 percent, more preferably at least about 80 or 90 percent, and most preferably at least about 95 percent of the nucleic acid probe length. When only a portion of the nucleic acid probe is intended to hybridize to the target nucleic acid molecule, that portion can be part of the first region, part of the second region, or spanning both the first and second regions. As used herein to describe the portion of the probe that hybridizes to a target nucleic acid, the phrase "substantially the entire length thereof" is intended to mean not more than two probe nucleotides, preferably not more than one probe nucleotide, that do not hybridize to the target over the length of the probe length.

Referring again to FIG. 1, while the probe remains in the hairpin conformation the fluorophore 18 bound to the second end of the nucleic acid probe is brought into sufficiently close proximity to the fluorescence quenching surface such that the surface substantially quenches fluorescent emissions by the fluorophore. In contrast, while the probe remains in the non-hairpin conformation, the fluorophore 18 bound to the second end of the nucleic acid probe is no longer constrained in proximity to the fluorescence quenching surface 12. As a result of its physical displacement away from the quenching surface, fluorescent emissions by the fluorophore 18 are substantially free of any quenching (i.e., emission from the sensor chip becomes detectable).

Selection of suitable nucleic acid molecules for use as probes can be achieved by (i) identifying an oligonucleotide that can hybridize to the target nucleic acid and then designing a nucleic acid probe that includes the oligonucleotide as a component part of the first and/or second region, and optionally as a component part of any loop region between the first and second regions; (ii) by identifying naturally occurring hairpin structures within the predicted folding structure of a target nucleic acid molecule, as described in co-pending U.S. Provisional Patent Application Ser. No. 60/533,894 to Miller et al., filed Jan. 2, 2004, now U.S. patent application Ser. No. 10/584,875 (as a national stage application of PCT/US2005/000053, filed Jan. 3, 2005), which is expressly incorporated by reference in its entirety; or (iii) using a combination of the above procedures, modifying a portion of a naturally occurring hairpin structure, e.g., modifying one or more bases in the first or second region to increase the stability of the resulting probe or the stability of the probe-target interaction.

The fluorescence quenching surface 18 is capable of quenching or absorbing the fluorescent emissions of the fluorophore within the desired bandwidth. The fluorescence quenching surface can exist as either a solid substrate or a coating applied to another (i.e., inert or functional) substrate. When the fluorescent quenching surface is applied to a substrate, the fluorescent quenching surface can exist over substantially the entire substrate or, alternatively, in a plurality of discrete locations on the substrate. To obtain the latter construction, the fluorescent quenching surface can either be applied to the substrate in only a few locations or, after applying to substantially the entire substrate, the fluorescence quenching material can be etched or removed from the substrate in all but the desired, discrete locations.

By way of example, sputtering of atoms or ions through a mask, photolithographic liftoff techniques, and electron beam lithography can be used. All three of these techniques can be used to pattern surfaces with fluorescence quenching agents in selected patterns with length scales as small as about 50 nm (or any larger patterns). Alternatively, soft lithography can be used to pattern the fluorescence quenching agent on the 500 nm scale and larger; or, also using soft lithography, the fluorescence quenching surface remains unmodified but the nucleic acid hairpins are applied thereto in a pattern using a spotter (i.e., spotting the buffer containing the hairpin) to make patterns on the 10 micron scale.

Preferred materials for formation of the fluorescence quenching surface include conductive metals or metal alloys, which offer the ability to completely or nearly completely quench the fluorescence emissions of the fluorophore, as well as semiconductor materials, either with or without n- or p-doping. Suitable conductive metals or metal alloys include, without limitation, gold, silver, platinum, copper, cobalt, iron, aluminum, iron-platinum, etc. Of these, gold, silver, and platinum are typically preferred. Suitable semiconductor materials include, without limitation, intrinsic or undoped silicon, p-doped silicon (e.g., $(CH_3)_2Zn$, $(C_2H_5)_2Zn$, $(C_2H_5)_2Be$, $(CH_3)_2Cd$, $(C_2H_5)_2Mg$, B, Al, Ga, or In dopants), n-doped silicon (e.g., $H_2Se$, $H_2S$, $CH_3Sn$, $(C_2H_5)_3S$, $SiH_4$, $Si_2H_6$, P, As, or Sb dopants), alloys of these materials with, for example, germanium in amounts of up to about 10% by weight, mixtures of these materials, and semiconductor materials based on Group III element nitrides. Other semiconductors known in the art can also be used.

The nucleic acid probe can be bound to the fluorescent quenching surface using known nucleic acid-binding chemistry or by physical means, such as through ionic, covalent or other forces well known in the art (see, e.g., Dattagupta et al., *Analytical Biochemistry* 177:85-89 (1989); Saiki et al., *Proc. Natl. Acad. Sci. USA* 86:6230-6234 (1989); Gravitt et al., *J. Clin. Micro.* 36:3020-3027 (1998), each of which is hereby incorporated by reference in its entirety). Either a terminal base or another base near the terminal base can be bound to the fluorescent quenching surface. For example, a terminal nucleotide base of the nucleic acid probe can be modified to contain a reactive group, such as (without limitation) carboxyl, amino, hydroxyl, thiol, or the like, thereby allowing for coupling of the nucleic acid probe to the surface.

The fluorophore can be any fluorophore capable of being bound to a nucleic acid molecule. Suitable fluorophores include, without limitation, fluorescent dyes, proteins, and semiconductor nanocrystal particles. The fluorophore used in the present invention is characterized by a fluorescent emission maxima that is detectable either visually or using optical detectors of the type known in the art. Fluorophores having fluorescent emission maxima in the visible spectrum are preferred.

Exemplary dyes include, without limitation, Cy2™, YO-PRO™-1, YOYO™-1, Calcein, FITC, FluorX™, Alexa™, Rhodamine 110, 5-FAM, Oregon Green™ 500, Oregon Green™ 488, RiboGreen™, Rhodamine Green™, Rhodamine 123, Magnesium Green™, Calcium Green™, TO-PRO™-1, TOTO®-1, JOE, BODIPY® 530/550, DiI, BODIPY® TMR, BODIPY® 558/568, BODIPY® 564/570, Cy3™, Alexa™ 546, TRITC, Magnesium Orange™, Phycoerythrin R&B, Rhodamine Phalloidin, Calcium Orange™, Pyronin Y, Rhodamine B, TAMRA, Rhodamine Red™, Cy3.5™, ROX, Calcium Crimson™, Alexa™ 594, Texas Red®, Nile Red, YO-PRO™-3, YOYO™-3, R-phycocyanin, C-Phycocyanin, TO-PRO™-3, TOTO®-3, DiD DilC(5), Cy5™, Thiadicarbocyanine, and Cy5.5™. Other dyes now known or hereafter developed can similarly be used as long as their excitation and emission characteristics are compatible with the light source and non-interfering with other fluorophores that may be present (i.e., not capable of participating in fluorescence resonant energy transfer or FRET).

Attachment of dyes to the opposite end of the nucleic acid probe can be carried using any of a variety of known techniques allowing, for example, either a terminal base or another base near the terminal base to be bound to the dye. For example, 3'-tetramethylrhodamine (TAMRA) may be attached using commercially available reagents, such as 3'-TAMRA-CPG, according to manufacturer's instructions (Glen Research, Sterling, Va.). Other exemplary procedures are described in, e.g., Dubertret et al., *Nature Biotech.* 19:365-370 (2001); Wang et al., *J. Am. Chem. Soc.,* 125:3214-3215 (2003); *Bioconjugate Techniques*, Hermanson, ed. (Academic Press) (1996), each of which is hereby incorporated by reference in its entirety.

Exemplary proteins include, without limitation, both naturally occurring and modified (i.e., mutant) green fluorescent proteins (Prasher et al., *Gene* 111:229-233 (1992); PCT Application WO 95/07463, each of which is hereby incorporated by reference in its entirety) from various sources such as *Aequorea* and *Renilla*; both naturally occurring and modified blue fluorescent proteins (Karatani et al., *Photochem. Photobiol* 55(2):293-299 (1992); Lee et al., *Methods Enzymol.* (*Biolumin. Chemilumin*) 57:226-234 (1978); Gast et al., *Biochem. Biophys. Res. Commun.* 80(1):14-21 (1978), each of which is hereby incorporated by reference in its entirety) from various sources such as *Vibrio* and *Photobacterium*; and phycobiliproteins of the type derived from cyanobacteria and eukaryotic algae (Apt et al., *J. Mol. Biol.* 238:79-96 (1995); Glazer, *Ann. Rev. Microbiol.* 36:173-198 (1982); Fairchild et al., *J. Biol. Chem.* 269:8686-8694 (1994); Pilot et al., *Proc. Natl. Acad. Sci. USA* 81:6983-6987 (1984); Lui et al., *Plant Physiol* 103:293-294 (1993); Houmard et al., *J. Bacteriol.* 170:5512-5521 (1988), each of which is hereby incorporated by reference in its entirety), several of which are commercially available from ProZyme, Inc. (San Leandro, Calif.). Other fluorescent proteins now known or hereafter developed can similarly be used as long as their excitation and emission characteristics are compatible with the light source and non-interfering with other fluorophores that may be present.

Attachment of fluorescent proteins to the opposite end of the nucleic acid probe can be carried using any of a variety of known techniques, for example, either a terminal base or another base near the terminal base can be bound to the fluorescent protein. Procedures used for tether dyes to the nucleic acid can likewise be used to tether the fluorescent protein thereto. These procedures are generally described in, e.g., *Bioconjugate Techniques*, Hermanson, ed. (Academic Press) (1996), which is hereby incorporated by reference in its entirety.

Nanocrystal particles or semiconductor nanocrystals (also known as Quantum Dot™ particles), whose radii are smaller than the bulk exciton Bohr radius, constitute a class of materials intermediate between molecular and bulk forms of matter. Quantum confinement of both the electron and hole in all three dimensions leads to an increase in the effective band gap of the material with decreasing crystallite size. Consequently, both the optical absorption and emission of semiconductor nanocrystals shift to the blue (higher energies) as the size of the nanocrystals gets smaller.

The core of the nanocrystal particles is substantially monodisperse. By monodisperse, it is meant a colloidal system in which the suspended particles have substantially identical size and shape, i.e., deviating less than about 10% in rms diameter in the core, and preferably less than about 5% in the core.

Particles size can be between about 1 nm and about 1000 nm in diameter, preferably between about 2 nm and about 50 nm, more preferably about 5 nm to about 20 nm (such as about 5, 6, 7, 8, 9, 10, 11, 12, 13, 14, 15, 16, 17, 18, 19, or 20 nm).

When capped nanocrystal particles of the invention are illuminated with a primary light source, a secondary emission of light occurs of a frequency that corresponds to the band gap of the semiconductor material used in the nanocrystal particles. The band gap is a function of the size of the nanocrystal particle. As a result of the narrow size distribution of the capped nanocrystal particles, the illuminated nanocrystal particles emit light of a narrow spectral range resulting in high purity light. Spectral emissions in a narrow range of no greater than about 60 nm, preferably no greater than about 40 nm and most preferably no greater than about 30 nm at full width half max (FWHM) are observed. Spectral emissions in even narrower ranges are most preferred.

The nanocrystal particles are preferably passivated or capped either with organic or inorganic passivating agents to eliminate energy levels at the surface of the crystalline material that lie within the energetically forbidden gap of the bulk interior. These surface energy states act as traps for electrons and holes that would normally degrade the luminescence properties of the material. Such passivation produces an atomically abrupt increase in the chemical potential at the interface of the semiconductor and passivating layer (Alivisatos, *J. Phys. Chem.* 100:13226 (1996), which is hereby incorporated by reference in its entirety). As a result, higher quantum efficiencies can be achieved.

Exemplary capping agents include organic moieties such as tri-n-octyl phosphine (TOP) and tri-n-octyl phosphine oxide (TOPO) (Murray et al., *J. Am. Chem. Soc.* 115:8706 (1993); Kuno et al., *J. Phys. Chem.* 106(23):9869 (1997), each of which is hereby incorporated by reference in its entirety), as well as inorganic moieties such as CdS-capped CdSe and the inverse structure (Than et al., *J. Phys. Chem.* 100:8927 (1996), which is hereby incorporated by reference in its entirety), ZnS grown on CdS (Youn et al., *J. Phys. Chem.* 92:6320 (1988), which is hereby incorporated by reference in its entirety), ZnS on CdSe and the inverse structure (Kortan et al., *J. Am. Chem. Soc.* 112:1327 (1990); Hines et al., *J. Phys. Chem.* 100:468 (1996), each of which is hereby incorporated by reference in its entirety), ZnSe-capped CdSe nanocrystals (Danek et al., *Chem. Materials* 8:173 (1996), which is hereby incorporated by reference in its entirety), and $SiO_2$ on Si (Wilson et al., *Science* 262:1242 (1993), which is hereby incorporated by reference in its entirety).

In general, particles passivated with an inorganic coating are more robust than organically passivated particles and have greater tolerance to processing conditions used for their incorporation into devices. Particles that include a "core" of one or more first semiconductor materials can be surrounded by a "shell" of a second semiconductor material.

Thus, the nanocrystal particles as used in the present invention can be formed of one or more semiconducting materials. Suitable semiconducting materials include, without limitation, a group IV material alone (e.g., Si and Ge), a combination of a group IV material and a group VI material, a combination of a group III material and a group V material, or a group II material and a group VI material. When a combination of materials are used, the semiconducting materials are presented in a "core/shell" arrangement.

Suitable core/shell material combinations include, without limitation, group IV material forming the core and group VI materials forming the shell; group III material forming the core and group V materials forming the shell; and group II material forming the core and group VI materials forming the shell. Exemplary core/shell combinations for groups IV/VI are: Pb and one or more of S, Se, and Te. Exemplary core/shell combinations for groups III/V are: one or more of Ga, In, and Al as the group III material and one or more of N, P, As, and Sb as the group V material. Exemplary core/shell combinations for groups II/VI are: one or more of Cd, Zn, and Hg as the group II material, and one or more of S, Se, and Te as the group VI material. Other combinations now known or hereinafter developed can also be used in the present invention.

Fluorescent emissions of the resulting nanocrystal particles can be controlled based on the selection of materials and controlling the size distribution of the particles. For example, ZnSe and ZnS particles exhibit fluorescent emission in the blue or ultraviolet range (~400 nm or less); Au, Ag, CdSe, CdS, and CdTe exhibit fluorescent emission in the visible spectrum (between about 440 and about 700 nm); InAs and GaAs exhibit fluorescent emission in the near infrared range (~1000 nm), and PbS, PbSe, and PbTe exhibit fluorescent emission in the near infrared range (i.e., between about 700-2500 nm). By controlling growth of the nanocrystal particles it is possible to produce particles that will fluoresce at desired wavelengths. As noted above, smaller particles will afford a shift to the blue (higher energies) as compared to larger particles of the same material(s).

Preparation of the Nanocrystal Particles can be Carried Out According to known procedures, e.g., Murray et al., *MRS Bulletin* 26(12):985-991 (2001); Murray et al., *IBM J. Res.*

Dev. 45(1):47-56 (2001); Sun et al., *J. Appl. Phys.* 85(8, Pt. 2A): 4325-4330 (1999); Peng et al., *J. Am. Chem. Soc.* 124 (13):3343-3353 (2002); Peng et al., *J. Am. Chem. Soc.* 124 (9):2049-2055 (2002); Qu et al., *Nano Lett* 1(6):333-337 (2001); Peng et al., *Nature* 404(6773):59-61 (2000); Talapin et al., *J. Am. Chem. Soc.* 124(20):5782-5790 (2002); Shevenko et al., *Advanced Materials* 14(4):287-290 (2002); Talapin et al., *Colloids and Surfaces, A: Physiochemical and Engineering Aspects* 202(2-3):145-154 (2002); Talapin et al., *Nano Lett.* 1(4):207-211 (2001), each of which is hereby incorporated by reference in its entirety.

Whether in a core/shell arrangement or otherwise passivated with other compounds, the nanocrystal particles can also be rendered water soluble, if so desired. To make water-soluble nanocrystal particles, hydrophilic capping compounds are bound to the particles. One suitable class includes carboxylic acid capping compounds with a thiol functional group (forming a sulfide bridge with the nanocrystal particle), which can be reacted with the nanocrystal. Exemplary capping compounds include, without limitation, mercaptocarboxylic acid, mercaptofunctionalized amines (e.g., aminoethanethiol-HCl, homocysteine, or 1-amino-2-methyl-2-propanethiol-HCl), mercaptofunctionalized sulfonates, mercaptofunctionalized alkoxides, mercaptofunctionalized phosphates and phosphonates, aminofunctionalized sulfonates, aminofunctionalized alkoxides, aminofunctionalized phosphates and phosphonates, phosphine(oxide)functionalized sulfonates, phosphine(oxide)functionalized alkoxides, phosphine(oxide)functionalized phosphates and phosphonates, and combinations thereof. Procedures for binding these capping compounds to the nanocrystal particles are known in the art, e.g., U.S. Pat. No. 6,319,426 to Bawendi et al., which is hereby incorporated by reference in its entirety.

Attachment of a nanocrystal particle to the opposite end of the nucleic acid probe can be carried using any of a variety of known techniques, for example, either a terminal base or another base near the terminal base can be bound to the nanocrystal particle. Procedure used for tether dyes to the nucleic acid can likewise be used to tether the nanocrystal particle thereto. Details on these procedures are described in, e.g., *Bioconjugate Techniques*, Hermanson, ed. (Academic Press) (1996), which is hereby incorporated by reference in its entirety.

Having identified the sequence of a nucleic acid molecule to be used as a probe in a sensor of the present invention, and having selected the appropriate fluorophore and fluorescence quenching surface to be utilized, the sensor of the present invention can be assembled using the above-described procedures. Attachment of the fluorophore to one end of the nucleic acid probe can be carried out prior to attachment of the opposite end of the nucleic acid probe to the fluorescence quenching surface, or vice versa. Alternatively, the probe can be ordered from any one of various vendors that specialize in preparing oligonucleotides to desired specifications (i.e., having one end modified for binding to the fluorescence quenching surface and the other end bound by a fluorophore) and thereafter attached to the fluorescence quenching surface. Two exemplary vendors are Midland Certified Reagent Co. (Midland, Tex.) and Integrated DNA Technologies, Inc. (Coralville, Iowa).

In preparing the sensor chips of the present invention, a competitor (or spacer) molecule can also be attached to the fluorescence quenching surface, either as a separate step or as a single step (i.e., using a solution containing both the nucleic acid probe and the competitor molecule). The role of the competitor molecule is simply to minimize the concentration (and promote dispersion) of nucleic acid probes bound to the fluorescence quenching surface, thereby inhibiting the likelihood of interference between adjacent nucleic acid probes, which could result in background fluorescence. Like the nucleic acid probes, the competitor molecule contains a reactive group such as (without limitation) carboxyl, amino, hydroxyl, thiol, or the like, thereby allowing for coupling of the competitor molecule to the fluorescence quenching surface. Preferred competitor molecules include, without limitation, thiol-containing compounds, such as mercaptopropanol, cysteine, thiooctic acid, 2-mercaptoethanol, 3-mercapto-2-butanol, 2-mercapto, 1,2-propanediol, 2-(butylamino)ethanethiol, 2-dimethylaminoethanethiol, 2-diethylaminoethanethiol, 3-mercaptopropionic acid, etc.

According to one approach, the fluorescence quenching surface is first exposed to a solution containing the competitor molecule and allowed to self-assemble (to the surface) for a sufficient length of time. Thereafter, the modified surface is secondly exposed to a solution containing the nucleic acid probe and allowed to self-assemble (to the surface) for a sufficient length of time. As is well known in the art, the exposure time to one or both of the solutions can vary according to the concentrations of the competitor molecule and the nucleic acid probe in their respective solutions. After each exposure, the fluorescence quenching surface can be rinsed with pure water or saline solution, preferably at elevated temperatures so as to remove unbound competitor or unbound nucleic acid probe, respectively.

According to another approach, the fluorescence quenching surface is simultaneously exposed to a solution containing both the competitor molecule and the nucleic acid probe, and allowed to self-assemble for a sufficient length of time. As noted above, the exposure time to the combined solution can vary according to the concentrations of the competitor molecule and the nucleic acid probe. After exposure, the fluorescence quenching surface can be briefly rinsed with pure water or saline solution, preferably at elevated temperatures so as to remove unbound competitor and/or unbound nucleic acid probe. The resulting sensor chip can then be used to detect the presence of target nucleic acid molecules in sample preparations.

The ratio of the competitor molecule to the nucleic acid probe is preferably between about 2:1 and about 18:1, more preferably between about 5:1 and about 15:1, most preferably between about 8:1 and about 12:1.

The sensor chip can have a number of configurations depending on the nature and number of target nucleic acid molecules to be identified by a single chip.

According to one embodiment, the sensor chip is constructed using one or more nucleic acid probes, whether the same or different, all of which are directed to the same target molecule (perhaps, however, at different locations on the target). In this case, the probes can be attached to the fluorescence quenching surface in any location or over the substantially entire surface thereof.

Figure 2:
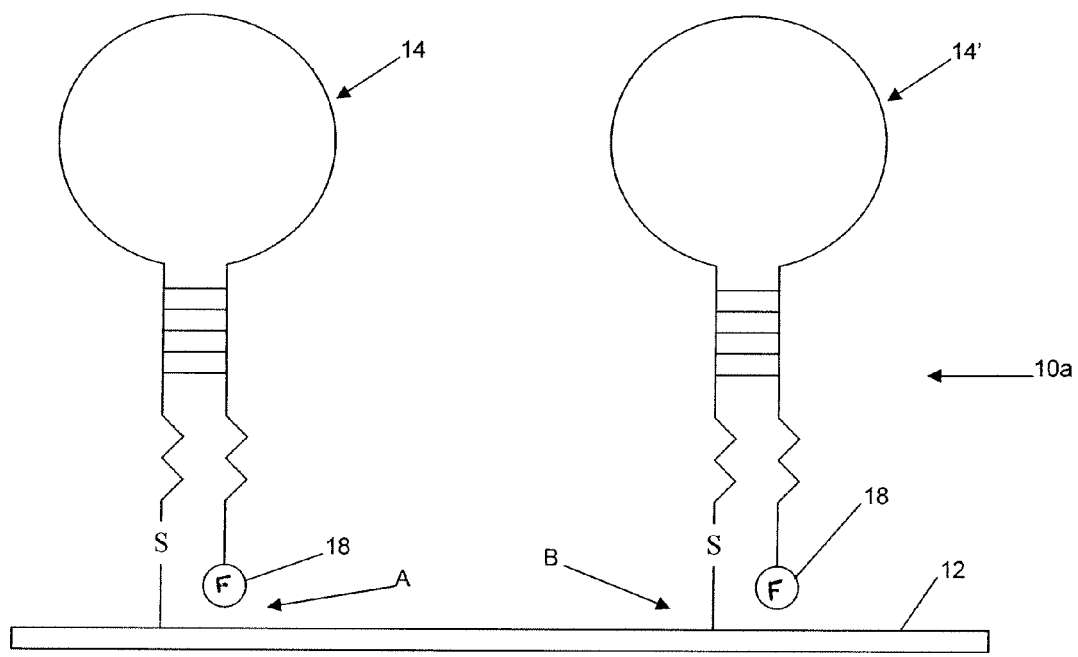
FIG. 2 illustrates one particular embodiment of the sensor chip, where two or more nucleic acid hairpin probes are bound to the fluorescent quenching surface so that they are present in discrete locations.

According to another embodiment, shown in FIG. 2, the sensor chip 10a is constructed using two or more nucleic acid probes 14,14' each having a different target nucleic acid molecule, where each of the two or more nucleic acid probes 14,14' is localized to a specific region A,B on the fluorescence quenching surface 12. One probe 14 (and its target) can be distinguished from another probe 14' (and its target) by the localization of any fluorescence emissions from the sensor chip 10a. In this arrangement, the fluorophores 18 used on the two or more nucleic acid probes 14,14' can be the same or they can be different.

Figure 3:
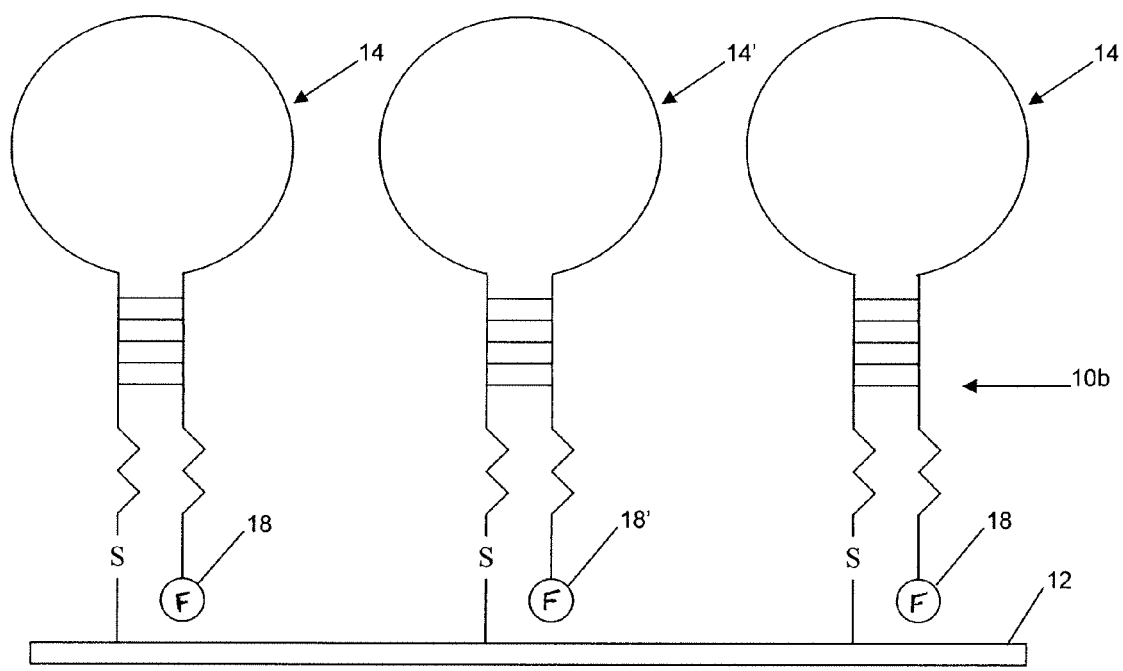
FIG. 3 illustrates another embodiment of the sensor chip, where two or more nucleic acid hairpin probes are bound to the fluorescent quenching surface so that they are co-localized. Different fluorophores having distinct fluorescent emissions distinguish one probe from another.

According to another embodiment, shown in FIG. 3, the sensor chip 10b is constructed using two or more nucleic acid probes 14,14' each having a different target nucleic acid molecule, where the two or more nucleic acid probes are co-localized (i.e., overlapping locations) over the fluorescence quenching surface 12 or portions thereof. In this arrangement, the fluorophores 18,18' used on the two or more nucleic acid probes are different so that fluorescent emissions from each can be distinguished from any others.

To distinguish between multiple fluorescent emissions emanating from a single location on the surface of the sensor chip (i.e., signal from one probe rather than another), the fluorescent emissions need only differ sufficiently to allow for resolution by the detector being utilized. Resolution of the signals can also depend, in part, on the nature of the emission pattern. For example, narrow emission maxima are more easily resolved than broad emission maxima that may interfere with emissions by other fluorophores. Thus, the selection of fluorophores should be made so as to minimize the interference given the sensitivity of the detector being utilized. By way of example, highly sensitive detectors can discriminate between the narrow emission maxima of semiconductor nanocrystals and dyes, allowing for separation of emission maxima that differ by about 1 nm or greater. Preferably, however, the emission maxima between the two or more fluorophores will differ by about 10 nm or greater or even 20 nm or greater, more preferably 30 nm or greater or even 40 nm or greater. Generally, the greater the separation between the emission maxima of the two or more fluorophores, the easier it will be to resolve their signals from overlapping locations on the surface of the sensor chip.

The sensor chip is intended to be used as a component in a biological sensor device or system. Basically, the device includes, in addition to the sensor chip, a light source that illuminates the sensor chip at a wavelength suitable to induce fluorescent emissions by the fluorophores associated with the one or more probes bound to the chip, and a detector positioned to capture any fluorescent emissions by the fluorophores.

The light source can be any light source that is capable of inducing fluorescent emissions by the selected fluorophores. Light sources that provide illumination wavelengths between about 200 nm and about 2000 nm are preferred. Exemplary light sources include, without limitation, lasers and arc lamps. Typical powers for lasers are at least about 1 mW; however, when used with an objective lens focusing the laser light to a small spot, as little as about 1 µW is sufficient. By way of example, Xenon arc lamps should be at least about 75 W.

The detector can be any detection device that is capable of receiving fluorescent emissions and generating a response to be examined by an operator of the biological sensor device. Suitable detectors include, without limitation, charge coupled devices (CCDs), photomultiplier tubes (PMTs), avalanche photodiodes (APDs), and photodiodes that contain a semiconductor material such as Si, InGaAs, extended InGaAs, Ge, HgCdTe, PbS, PbSe, or GaAs to convert optical photons into electrical current. Of these suitable detectors, the CCD is preferred because it can produce an image in extremely dim light, and its resolution (i.e., sharpness or data density) does not degrade in low light.

In addition to the above components, the biological sensor device can also include a notch filter positioned between the light source and the sensor chip and/or a bandpass filter positioned between the sensor chip and the detector. The notch filter will screen out a narrow band of photoradiation, i.e., at or near the excitation maxima of the selected fluorophore(s), so as to minimize any background excitation by materials present in or on the sensor chip or by non-quenched fluorophore(s). The bandpass filters control the spectral composition of transmitted energy, typically though not exclusively by the effects of interference, resulting in high transmission over narrow spectral bands. By way of example, the bandpass filter can allow passage of light within a range that is not more than about 10 nm greater or less than the wavelength of the maximum emissions of the fluorophore(s). When two or more fluorophores are used having different emission maxima, the bandpass filter will emit passage of light within a larger wavelength band that extends from slightly below than the lowest wavelength maxima up to slightly higher than the highest wavelength maxima. Alternatively, when multiple fluorophores are used the emission signal can be split prior to passage through any filters (i.e., one for each fluorophore). Each split emission signal can include a separate bandpass filter that is configured for the emission maxima of one fluorophore but not the others.

Figure 4:
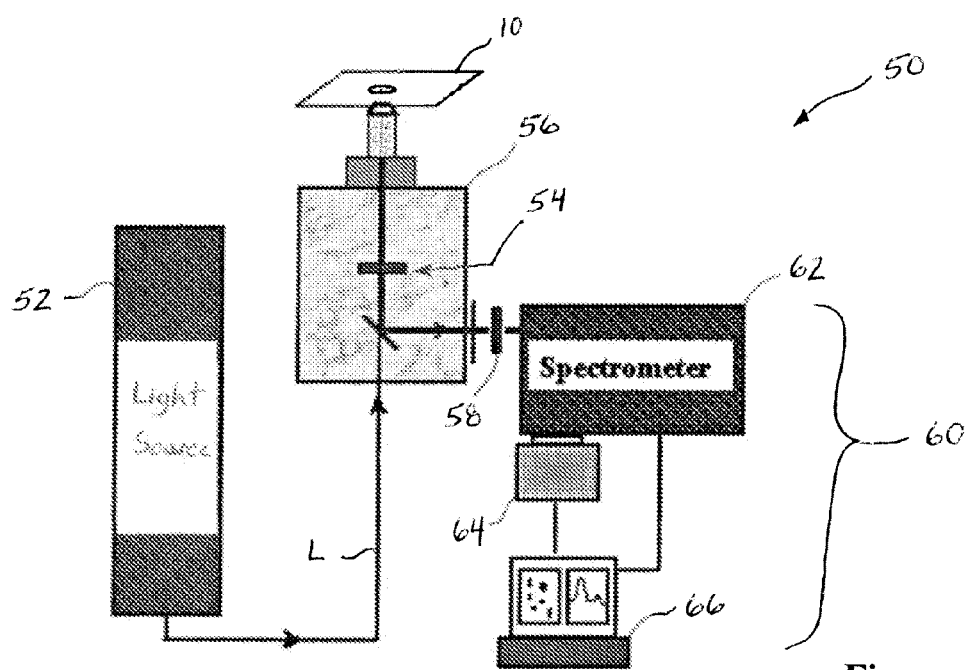
FIG. 4 is a schematic showing a biological detection device according to one embodiment of the present invention, which includes, inter alia, an inverted fluorescence microscope equipped with a liquid nitrogen cooled charge coupled device (CCD).

By way of example, FIG. 4 shows the configuration of one particular embodiment of the biological sensor device 50. The device includes a light source 52 that produces a focused beam of light L which is directed through a notch filter 54 and through an inverted microscope 56 (as shown, the notch filter is a component of the inverted microscope), where it contacts the sensor chip 10 placed on a sample stage. Any fluorescent emissions are captured by the inverted microscope 56 and the signal passes through a bandpass filter 58 prior to reaching the detector device 60. As shown, the detector device 60 includes a spectrophotometer 62 coupled to a CCD 64, whose electrical output signal is directed to a personal computer 66 or similar device capable of receiving the electrical output and generating an image of the detected fluorescence emitted from the sensor chip 10.

The sample is preferably present in the form of a buffered solution or other medium suitable for use during hybridization. The sample itself can be either a clinical or environmental sample to which buffer or buffer salts are added, derived from purification of DNA or RNA from clinical or environmental specimens, or the product of a PCR reaction, etc. Basically, the sample can be in any form where the suspected nucleic acid target is maintained in a substantially stable manner (i.e., without significant degradation).

During use of the biological sensor device and the associated sensor chip, the presence of a target nucleic acid molecule in a sample can be achieved by first exposing the sensor chip to a sample under conditions effective to allow any target nucleic acid molecule in the sample to hybridize to the first and/or second regions of the nucleic acid probe(s) present on the sensor chip, illuminating the sensor chip with light sufficient to cause emission of fluorescence by the fluorophore(s), i.e., associated with the nucleic acid probe(s), and then determining whether or not the sensor chip emit(s) detectable fluorescent emission (of the fluorophore(s)) upon said illuminating. When fluorescent emission by the fluorophore(s) is detected from the chip, such detection indicates that the nucleic acid probe is in the non-hairpin conformation and therefore that the target nucleic acid molecule is present in the sample.

The conditions utilized during the exposure step include hybridization and then wash conditions, as is typical during hybridization procedures. The hybridization and wash conditions can be carried in buffered saline solutions either at or slightly above room temperature (i.e., up to about 30° C.). Alternatively, as is known in the art, the hybridization conditions can be selected so that stringency will vary. That is, lower stringency conditions will discriminate less between perfectly matched target nucleic acid molecules and non-perfectly matched nucleic acid molecules, whereas higher stringency conditions will discriminate between perfectly matched and non-perfectly matched nucleic acid molecules. In general, the highest stringency that can be tolerated by the probe and the intended target can be selected so as to minimize or completely avoid the possibility of a false positive response caused by hybridization to non-perfectly matched nucleic acid molecules. Alternatively, it may be desirable to begin hybridization at a temperature above the melting temperature of the hairpin probe, thus promoting an open conformation, and then during the course of the hybridization procedure allowing the chip to cool so that hairpins not participating in hybridization (i.e., in cases where there is no complementarity) to re-fold, and fluorescence to be quenched. The latter procedure would be desirable, for example, when the hairpin probe is quite stable (having a predicted E value in the range of about −9 to about −12 kcal/mol), even in the presence of target nucleic acid molecules. In either case though, detection typically is not carried out until the hybridization and wash procedures have been completed.

An example of suitable stringency conditions is when hybridization is carried out at a temperature of at least about 35° C. using a hybridization medium that includes about 0.3M Na$^+$, followed by washing at a temperature of at least about 35° C. with a buffer that includes about 0.3M Na$^+$ or less. Higher stringency can readily be attained by increasing the temperature for either hybridization or washing conditions or decreasing the sodium concentration of the hybridization or wash medium. Other factors that affect the melting temperature of the hairpin probe include its GC content and the length of the stem (and whether the stem perfectly hybridizes intramolecularly). Nonspecific binding may also be controlled using any one of a number of known techniques such as, for example, addition of heterologous RNA, DNA, and SDS to the hybridization buffer, treatment with RNase, etc. Wash conditions can be performed at or below stringency of the hybridization procedure, or even at higher stringency when so desired. Exemplary high stringency conditions include carrying out hybridization at a temperature of about 50° C. to about 65° C. (from about 1 hour up to about 12 hours) in a hybridization medium containing 2×SSC buffer (or its equivalent), followed by washing carried out at between about 50° C. to about 65° C. in a 0.1×SSC buffer (or its equivalent). Variations on the hybridization conditions can be carried out as described in Sambrook et al., *Molecular Cloning: A Laboratory Manual*, Second Edition, Cold Spring Harbor Press, NY (1989), which is hereby incorporated by reference in its entirety.

The nucleic acid probes, used in preparing sensor chips of the present invention, can be selected so that they hybridize to target nucleic acid molecules that are specific to pathogens, are associated with disease states or conditions, contain polymorphisms that may or may not be associated with a disease state but can also be a forensic target or associated with a breeding trait for plants or animal. Other uses should be appreciated by those of ordinary skill in the art.

Figure 5:
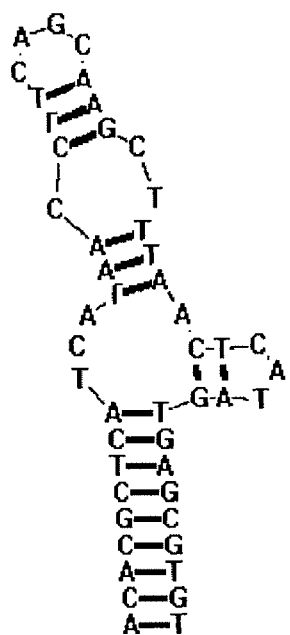
FIG. 5 illustrates the predicted folding structure of the nucleotide sequence for hairpin H1 (SEQ ID NO: 1), which was designed to incorporate portions of the *Staphylococcus aureus* FemA methicillin-resistance gene (Berger-Bachi et al., *Mol. Gen. Genet.* 219:263-269 (1989); Genbank accession X17688, each of which is hereby incorporated by reference in its entirety). The folding structure was predicted using the computer program RNAStructure version 3.7 (Mathews et al., *J. Mol Biol* 288:911-940 (1999), which is hereby incorporated by reference in its entirety) and later confirmed by melting experiments.
Figure 6:
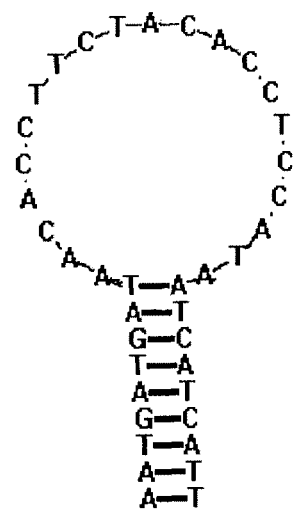
FIG. 6 illustrates the predicted folding structure of the nucleotide sequence for hairpin H2 (SEQ ID NO: 2), which was designed to incorporate portions of the *Staphylococcus aureus* mecR methicillin-resistance gene (Archer et al., *Antimicrob. Agents. Chemother.* 38:447-454 (1994), which is hereby incorporated by reference in its entirety). The folding structure was predicted using the computer program RNAStructure version 3.7 (Mathews et al., *J. Mol. Biol.* 288:911-940 (1999), which is hereby incorporated by reference in its entirety) and later confirmed by melting experiments.
Figures 7A, 7B:
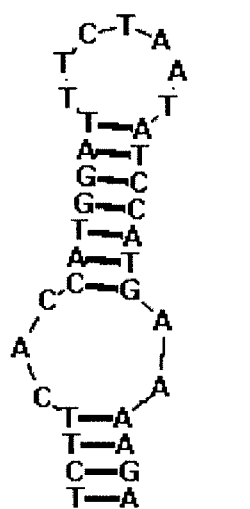
FIGS. 7A-B illustrate the secondary structure of hairpin HP1 alone (7A) and the hybrid HP1-T1 (7B). HP1 corresponds to SEQ ID NO: 7, which is targeted to a complementary sequence T1 (SEQ ID NO: 11) that is substantially homologous to *Bacillus anthracis* pag. The folding structure was predicted using the computer program RNAStructure version 3.7 (Mathews et al., *J. Mol. Biol.* 288:911-940 (1999), which is hereby incorporated by reference in its entirety).
Figure 8A:
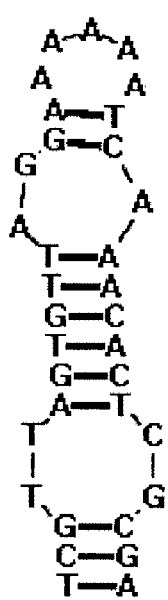
FIGS. 8A-B illustrate the secondary structure of hairpin HP2 alone (8A) and the hybrid HP2-T2 (8B). HP2 corresponds to SEQ ID NO: 5, which is targeted to a complementary sequence T2 (SEQ ID NO: 12) that is substantially homologous to *Bacillus anthracis* pag. The folding structure was predicted using the computer program RNAStructure version 3.7 (Mathews et al., *J. Mol. Biol.* 288:911-940 (1999), which is hereby incorporated by reference in its entirety).
Figure 8B:
Figure 9:
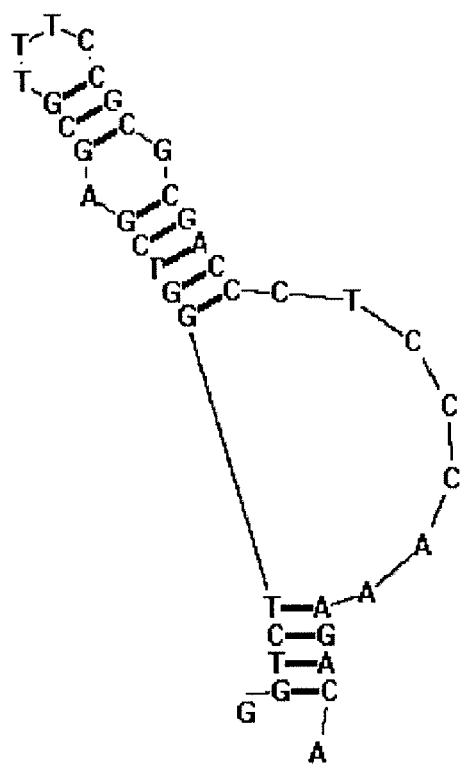
FIG. 9 illustrates the secondary structure shows the CCD image post-hybridization. A clear signal, distinct of background, is obtained following hybridization of T1 to H1.
Figure 10:
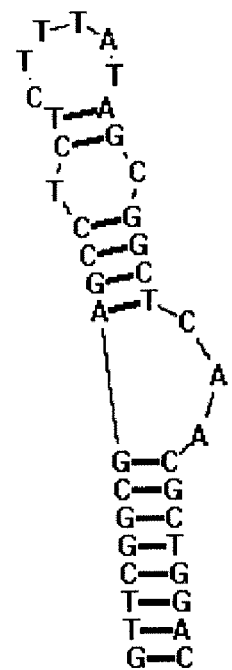
Figure 11A:
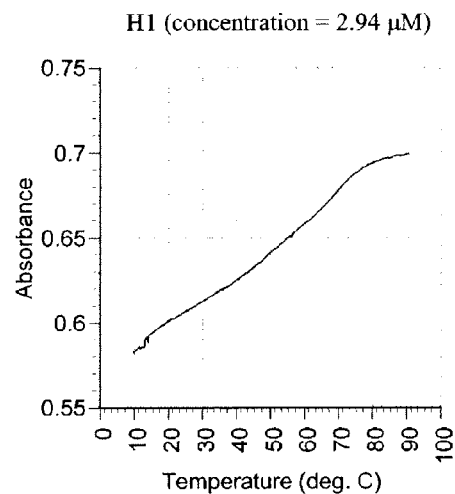
Figure 11B:
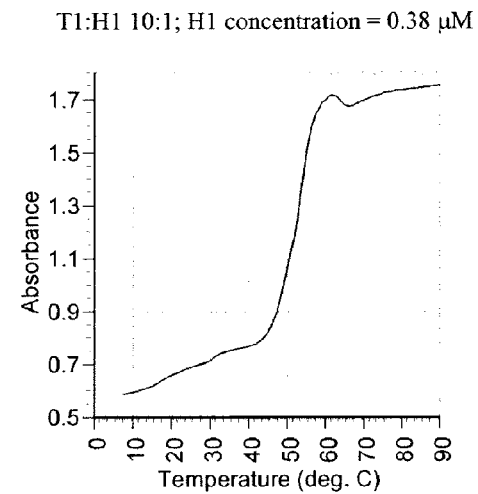
Figure 11C:
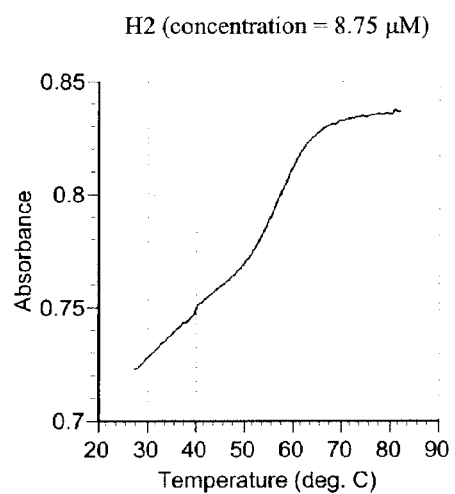
Figure 11D:
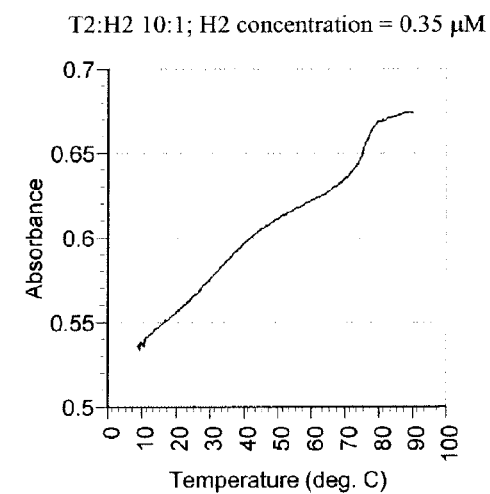
Figure 21:
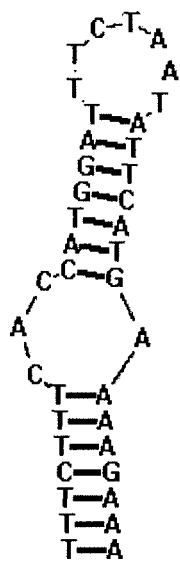
FIG. 21 illustrates the secondary structure of a hairpin (SEQ ID NO: 6) targeted to *Bacillus anthracis* pag. The folding structure was predicted using the computer program RNAStructure version 3.7 (Mathews et al., *J. Mol. Biol.* 288.
Figure 22:
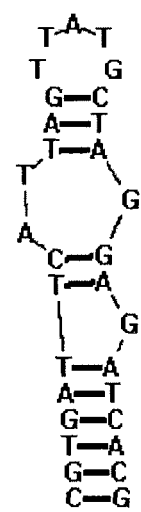
Figure 23:
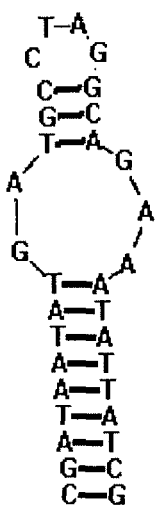
Figure 24:
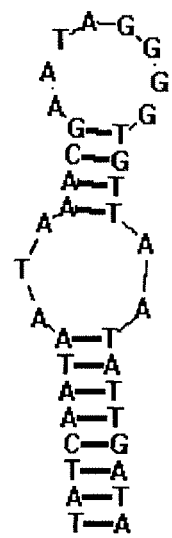
Figure 26:
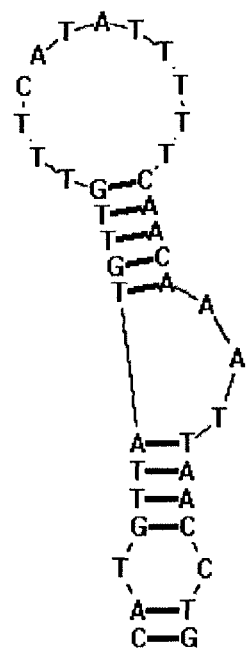

By way of example, a number of specific nucleic acid probes have been identified. The nucleotide sequences and their targets are identified below:

SEQ ID NO: 1 (targeted to *Staphylococcus aureus* FemA) has the nucleotide sequence acacgctcatcataaccttcagcaagctttaactcatagtgagcgtgt and is characterized by the putative folding structure illustrated in FIG. 5;

SEQ ID NO: 2 (targeted to *Staphylococcus aureus* mecR) has the nucleotide sequence aatgatgataacaccttctacacctccataatcatcatt and is characterized by the putative folding structure illustrated in FIG. 6;

SEQ ID NO: 3 (targeted to *Exophiala dermatitidis* 18S ribosomal RNA gene) has the nucleotide sequence ggtctggtcgagcgtttccgcgcgaccctcccaaagaca and is characterized by the putative folding structure illustrated in FIG. 9;

SEQ ID NO: 4 (targeted to *Trichophyton tonsurans* strain 18S ribosomal RNA gene) has the nucleotide sequence gttcggcgagcctctctttatagcggctcaacgctggac and is characterized by the putative folding structure illustrated in FIG. 10;

SEQ ID NO: 5 (targeted to *Bacillus anthracis* pag) has the nucleotide sequence tcgttagtgttaggaaaaaatcaaacactcgcga and is characterized by the putative folding structure illustrated in FIG. 8A;

SEQ ID NO: 6 (targeted to *Bacillus anthracis* pag) has the nucleotide sequence tttctttcaccatggatttctaatattcatgaaaagaaa and is characterized by the putative folding structure illustrated in FIG. 21;

SEQ ID NO: 7 (targeted to *Bacillus anthracis* pag) has the nucleotide sequence tcttcaccatggatttctaatatccatgaaaaga and is characterized by the putative folding structure illustrated in FIG. 7A;

SEQ ID NO: 8 (targeted to *Bacillus cereus* isoleucyl-tRNA synthetase (ileS1) gene) has the nucleotide sequence cgtgattcattagttatgctaggagatcacg and is characterized by the putative folding structure illustrated in FIG. 22;

SEQ ID NO: 9 (targeted to a portion of *Staphylococcus aureus* complete genome located between ORFID:SA0529 and ORFID:SA0530) has the nucleotide sequence cgataatatgatgcctaggcagaaatattatcg and is characterized by the putative folding structure illustrated in FIG. 23;

SEQ ID NO: 10 (targeted to a portion of *Staphylococcus aureus* complete genome located between ORFID:SA0529 and ORFID:SA0530 and including several bases within the latter open reading frame) has the nucleotide sequence tatcaataataaacgaataggggtgttaatattgata and is characterized by the putative folding structure illustrated in FIG. 24;

SEQ ID NO: 20 (targeted to *Staphylococcus aureus* mecR) has the nucleotide sequence caggttaatttgaaaaatatgaaacaacataacatg and is characterized by the putative folding structure illustrated in FIG. 25;

SEQ ID NO: 21 (targeted to *Staphylococcus aureus* mecR) has the nucleotide sequence catgttatgttgtttcatattttcaacaaattaacctg and is characterized by the putative folding structure illustrated in FIG. 26;

SEQ ID NO: 22 (targeted to *Staphylococcus aureus* genome, ORFID:SA4_9) has the nucleotide sequence gataatatgatgcctaggcagaaatattatc and is characterized by the putative folding structure illustrated in FIG. 31;

SEQ ID NO: 23 (targeted to *Staphylococcus aureus* genome, ORFID:SA4_9B) has the nucleotide sequence gataatatttctgcctaggcatcatattatc and is characterized by the putative folding structure illustrated in FIG. 32;

SEQ ID NO: 24 (targeted to *Staphylococcus aureus* genome, ORFID:SA4_7 BH) has the nucleotide sequence atatcaataataaacgaatagggtgttaatattgatat and is characterized by the putative folding structure illustrated in FIG. 33;

SEQ ID NO: 25 (targeted to *Staphylococcus aureus* genome, ORFID:SA4_7 BHB) has the nucleotide sequence atatcaatattaacacccctattcgtttattattgatat and is characterized by the putative folding structure illustrated in FIG. 34;

SEQ ID NO: 26 (targeted to *Staphylococcus aureus* genome, ORFID:SA4_15) has the nucleotide sequence gtgatgtattagaaagaaatttataataaatcac and is characterized by the putative folding structure illustrated in FIG. 35;

SEQ ID NO: 27 (targeted to *Staphylococcus aureus* genome, ORFID:SA4_15B) has the nucleotide sequence gtgatttattataaatttctttctaatacatcac and is characterized by the putative folding structure illustrated in FIG. 36;

SEQ ID NO: 28 (rpoB 147 sense, targeted to *S. epidermidis*) has the nucleotide sequence gcagagttaacgcacaaacgtcgtttatctgc and is characterized by the putative folding structure illustrated in FIG. 37;

SEQ ID NO: 29 (rpoB 147 antisense, targeted to *S. epidermidis*) has the nucleotide sequence gcagataaacgacgtttgtgcgttaactctgc and is characterized by the putative folding structure illustrated in FIG. 38;

SEQ ID NO: 30 (rpoB 205 sense, targeted to *S. epidermidis*) has the nucleotide sequence aacgtgctcaaatggaagtgcgtgacgtt and is characterized by the putative folding structure illustrated in FIG. 39;

SEQ ID NO: 31 (rpoB 205 antisense, targeted to *S. epidermidis*) has the nucleotide sequence aacgtcacgcacttccatttgagcacgtt and is characterized by the putative folding structure illustrated in FIG. 40;

SEQ ID NO: 32 (dnaJ 465 sense, targeted to *S. sciuri*) has the nucleotide sequence cttgtacgtactgtaacggacaag and is characterized by the putative folding structure illustrated in FIG. 41;

SEQ ID NO: 33 (dnaJ 465 antisense, targeted to *S. sciuri*) has the nucleotide sequence

```
cttgtccgttacagtacgtacaag
``` and is characterized by the putative folding structure illustrated in FIG. 42;

SEQ ID NO: 34 (dnaJ 546 sense, targeted to *S. sciuri*) has the nucleotide sequence

```
gtcctgaatgtgaaggttctggac
``` and is characterized by the putative folding structure illustrated in FIG. 43;

SEQ ID NO: 35 (dnaJ 546 antisense, targeted to *S. sciuri*) has the nucleotide sequence

```
gtccagaaccttcacattcaggac
``` and is characterized by the putative folding structure illustrated in FIG. 44; and SEQ ID NO: 36 (dnaJ 681 sense, targeted to *S. sciuri*) has the nucleotide sequence

```
tagctggtaaaggtggtccaggta
``` and is characterized by the putative folding structure illustrated in FIG. 45.

Pathogens that can be identified using the products and processes of the present invention include any bacteria, fungi, viruses, rickettsiae, chlamydiae, and parasites, but preferably those identified as belonging within the classifications listed as Biosafety Levels Two, Three, and Four by the U.S. Centers for Disease Control and Prevention, the National Institutes of Health, and the World Health Organization.

Exemplary bacterial pathogen that can be identified in accordance with the present invention include, without limitation: *Acinetobacter calcoaceticus, Actinobacillus* species (all species), *Aeromonas hydrophila, Amycolata autotrophica, Arizona hinshawii* (all serotypes), *Bacillus anthracis, Bartonella* species (all species), *Brucella* species (all species), *Bordetella* species (all species), *Borrelia* species (e.g., *B. recurrentis, B. vincenti*), *Campylobacter* species (e.g., *C. fetus, C. jejuni*), *Chlamydia* species (e.g., *Chl. psittaci, Chl. trachomatis*), *Clostridium* species (e.g., *Cl. botulinum, Cl. chauvoei, Cl. haemolyticum, Cl. histolyticum, Cl. novyi, Cl. septicum, Cl. tetani*), *Corynebacterium* species (e.g., *C. diphtheriae, C. equi, C. haemolyticum, C. pseudotuberculosis, C. pyogenes, C. renale*), *Dermatophilus congolensis, Edwardsiella tarda, Erysipelothrix insidiosa, Escherichia coli* (e.g., all enteropathogenic, enterotoxigenic, enteroinvasive and strains bearing K1 antigen), *Francisella tularensis, Haemophilus* species (e.g., *H. ducreyi, H. influenzae*), *Klebsiella* species (all species), *Legionella pneumophila, Leptospira interrogans* (e.g., all serotypes), *Listeria* species (all species), *Moraxella* species (all species), *Mycobacteria* species (all species), *Mycobacterium avium, Mycoplasma* species (all species), *Neisseria* species (e.g., *N. gonorrhoea, N. meningitides*), *Nocardia* species (e.g., *N. asteroides, N. brasiliensis, N. otitidiscaviarum, N. transvalensis*), *Pasteurella* species (all species), *Pseudomonas* species (e.g., *Ps. mallei, Ps. pseudomallei*), *Rhodococcus equi, Salmonella* species (all species), *Shigella* species (all species), *Sphaerophorus necrophorus, Staphylococcus aureus, Streptobacillus moniliformis, Streptococcus* species (e.g., *S. pneumoniae, S. pyogenes*), *Treponema* species (e.g., *T. carateum, T. pallidum*, and *T. pertenue*), *Vibrio* species (e.g., *V. cholerae, V. parahemolyticus*), and *Yersinia* species (e.g., *Y. enterocolitica, Y. pestis*).

Exemplary fungal pathogens that can be identified in accordance with the present invention include, without limitation: *Blastomyces dermatitidis, Cryptococcus neoformans, Paracoccidioides braziliensis, Trypanosoma cruzi, Coccidioides immitis, Pneumocystis carinii*, and *Histoplasma* species (e.g., *H. capsulatum, H. capsulatum* var. *duboisifi*).

Exemplary parasitic pathogens that can be identified in accordance with the present invention include, without limitation: *Endamoeba histolytica, Leishmania* species (all species), *Naegleria gruberi, Schistosoma mansoni, Toxocara canis, Toxoplasma gondii, Trichinella spiralis*, and *Trypanosoma cruzi*.

Exemplary viral, rickettsial, and chlamydial pathogens that can be identified in accordance with the present invention include, without limitation: Adenoviruses (all types), Cache Valley virus, Coronaviruses, Coxsackie A and B viruses, Cytomegaloviruses, Echoviruses (all types), Encephalomyocarditis virus (EMC), Flanders virus, Hart Park virus, Hepatitis viruses-associated antigen material, Herpesviruses (all types), Influenza viruses (all types), Langat virus, Lymphogranuloma venereum agent, Measles virus, Mumps virus, Parainfluenza virus (all types), Polioviruses (all types), Poxviruses (all types), Rabies virus (all strains), Reoviruses (all types), Respiratory syncytial virus, Rhinoviruses (all types), Rubella virus, Simian viruses (all types), Sindbis virus, Tensaw virus, Turlock virus, Vaccinia virus, Varicella virus, Vesicular stomatitis virus, *Vole rickettsia*, Yellow fever virus, Avian leukosis virus, Bovine leukemia virus, Bovine papilloma virus, Chick-embryo-lethal orphan (CELO) virus or fowl adenovirus 1, Dog sarcoma virus, Guinea pig herpes virus, Lucke (Frog) virus, Hamster leukemia virus, Marek's disease virus, Mason-Pfizer monkey virus, Mouse mammary tumor virus, Murine leukemia virus, Murine sarcoma virus, Polyoma virus, Rat leukemia virus, Rous sarcoma virus, Shope fibroma virus, Shope papilloma virus, Simian virus 40 (SV-40), Epstein-Barr virus (EBV), Feline leukemia virus (FeLV), Feline sarcoma virus (FeSV), Gibbon leukemia virus (GaLV), Herpesvirus (HV) ateles, Herpesvirus (HV) saimiri, Simian sarcoma virus (SSV)-1, Yaba, Monkey pox virus, Arboviruses (all strains), Dengue virus, Lymphocytic choriomeningitis virus (LCM), *Rickettsia* (all species), Yellow fever virus, Ebola fever virus, Hemorrhagic fever agents (e.g., Crimean hemorrhagic fever, (Congo), Junin, and Machupo viruses, Herpesvirus simiae (Monkey B virus), Lassa virus, Marburg virus, Tick-borne encephalitis virus complex (e.g., Russian spring-summer encephalitis, Kyasanur forest disease, Omsk hemorrhagic fever, and Central European encephalitis viruses), and Venezuelan equine encephalitis virus.

Thus, a further aspect of the present invention relates to a method of detecting presence of a pathogen in a sample that is carried out by performing the above-described method (of detecting the presence of the target nucleic acid molecule) when using a sensor chip having a nucleic acid probe with at least portions of the first and/or second region thereof specific for hybridization with a target nucleic acid molecule of a pathogen.

Yet another aspect of the present invention relates to a method of genetic screening that is carried out by performing the above-described method (of detecting the presence of the target nucleic acid molecule) when using a sensor chip having a nucleic acid probe with at least portions of the first and/or second region thereof specific for hybridization with a genetic marker. As noted above, the genetic marker can be associated with disease states or conditions, contain polymorphisms that may or may not be associated with a disease state but can also be a forensic target or associated with a breeding trait for plants or animal

EXAMPLES

The following examples are provided to illustrate embodiments of the present invention but are by no means intended to limit its scope.

Example 1

Predicted Secondary Structure of H1 and H2

Two DNA hairpins, H1 and H2 (Table 1 below), were designed to incorporate portions of the *Staphylococcus areus* FemA (Berger-Bachi et al., *Mol. Gen. Genet.* 219:263-269 (1989); Genbank accession X17688, each of which is hereby incorporated by reference in its entirety) and mecR (Archer et al., *Antimicrob. Agents. Chemother.* 38:447-454 (1994), which is hereby incorporated by reference in its entirety) methicillin-resistance genes, and bearing a 5' end-linked thiol and a 3' end-linked rhodamine. After designing the nucleic acid molecules H1 and H2, they were ordered from Midland Certified Reagent Co. (GF-grade), and used as supplied.

TABLE 1

Sequences used in Examples 1-4

| Entry | SEQ ID NO: | Sequence |
|---|---|---|
| H1 | 1 | (C6Thiol)-acacgctcatcataaccttcagcaagcttta actcatagtgagcgtgt-Rhodamine |
| T1 | 11 | acgctcactatgagttaaagcttgctgaaggttatga |
| H2 | 2 | (C6Thiol)-aatgatgataacaccttctacacctccataa tcatcatt-Rhodamine |
| T2 | 12 | tatggaggtgtagaaggtgttatcatcatt |

Both H1 and H2, and their respective complementary strands T1 and T2, were obtained from a commercial supplier.

The computer program RNAStructure version 3.7 (Mathews et al., *J. Mol. Biol.* 288:911-940 (1999), which is hereby incorporated by reference in its entirety) was used to predict the secondary structures of H1 and H2 prior to synthesis. Predicted lowest energy structures (using parameters derived from Santa Lucia, Jr., *Proc. Natl. Acad. Sci. USA* 95:1460-1465 (1998), which is hereby incorporated by reference in its entirety) are shown in FIGS. 5 and 6, respectively. These computational predictions of the hairpin secondary structure for H1 and H2 were confirmed through thermal melting experiments.

All thermal melts were conducted on a Gilford spectrophotometer, with the oligonucleotide dissolved in 0.5 M NaCl Buffer (20 mM cacodylic acid and 0.5 mM EDTA, 0.5 M NaCl, pH=7; all $H_2O$ used in the preparation of buffers was 18.2 MΩ, as produced by a Barnstead Nanopure system). Each sample was warmed to 80° C., then cooled back to 10° C. prior to running the melting experiment. Results are shown in FIGS. 11A-D. Measured melting temperatures of H1 and H2 were 69° C. and 58° C., respectively.

Example 2

Preparation of Substrate and DNA Immobilization

Glass slides were cleaned with piranha etch solution (4:1 concentrated $H_2SO_4$/30% $H_2O_2$) overnight at room temperature, and then rinsed with ultrapure water. Metal deposition was performed at a rate of 0.2 nm/s using Denton Vacuum Evaporator (DV-502A). First, a chromium adhesion layer of 7 nm was coated on the glass, followed by 100 nm thick gold film. Before use, the gold substrates were annealed at 200° C. for one hour and cleaned with piranha solution for 0.5 hr.

The gold-coated substrate was soaked in a mixture solution of hairpin oligonucleotide and 3-mercapto-1-propanol (MP) (Aldrich Chemical Company, used without further purification) at a ratio of 1 to 10 for self-assembly. Two hours later, the substrate was thoroughly rinsed with hot water (90° C. or higher; $H_2O$ used in the rinse solution was 18.2 MΩ, as produced by a Barnstead Nanopure system) to remove unbound DNA. Next, the substrate carrying the mixed monolayer was immersed in 0.5 M NaCl buffer (20 mM Cacodylic acid, 0.5 mM EDTA, 0.5 M NaCl, pH=7). Optimization of both the DNA to MP ratio and the immersion time were useful in obtaining the most efficient increase in fluorescence intensity. Longer incubation times and lower relative concentrations of MP would be expected to result in Au surfaces with larger amounts of bound DNA. However, these conditions should also lead to complications resulting from nonspecific adhesion of DNA to the surface (Gearhart et al., *J. Phys. Chem. B* 105:12609-12615 (2001), which is hereby incorporated by reference in its entirety), or by a lack of sufficient interstitial space for high hybridization efficiency (Lin et al., *J. Langmuir* 18:788-796 (2002), which is hereby incorporated by reference in its entirety). Indeed, as described in greater detail below, it was found that significant deviation from the conditions described above can result in significant background fluorescence intensity.

A number of different MP:probe solutions were prepared and allowed to self-assemble to gold-coated substrate. Thereafter, the resulting sensor chips were examined for their fluorescence efficiency (i.e., comparing pre- and post-hybridization fluorescence).

TABLE 2

Relationship of MP:Probe Concentration Ratio and Chip Performance

| Probe conc. (µM) | MP:Probe Ratio | Fold-Increase in Chip Fluorescence | Comment |
|---|---|---|---|
| 0.13 | 0:1 | 0.73 | Background signal is 4 times higher than with MP |
| 0.13 | 1:1 | 1.53 | Low FL intensity |
| 0.13 | 5:1 | 5.13 | Good FL intensity |
| 0.13 | 10:1 | 23.7 | Near optimal FL intensity |
| 0.13 | 20:1 | 1.95 | Low FL intensity |
| 0.13 | 30:1 | 1.87 | Low FL intensity |

To achieve a higher fold-increase in fluorescence for post-hybridization relative to pre-hybridization, there should be a lower background signal and, thus, better quenching efficiency. In addition, high hybridization efficiency is desirable, which means that most hairpins on the surface form a duplex in the presence of the target. MP was used as a competitor (i.e., spacer) molecule for binding to the surface of the chip. In the absence of such a competitor (i.e, 0:1 ratio), the probes were densely packed on the chip surface and, as a result, there was not enough interstitial space for them to form hairpin configuration and non-specific binding could not be avoided. Consequently, quenching of fluorophores by gold is poor, resulting in higher background signal. In contrast, when the competitor is present in too high a ratio (i.e., 20:1 or greater), the competitor will have superiority to bind the chip surface. As a result, this leads to not enough probes and lower signal during post-hybridization detection. Optimal MP:probe ratio provides enough space for duplex formation during hybridization and results in improved performance of the chip.

Example 3

Construction of Fluorescent Detection System Using H1- and H2-Functionalized Gold Fluorescence measurement was performed on a Nikon inverted fluorescence microscope equipped with a liquid nitrogen cooled charge coupled device (CCD) (FIG. 4). An Ar+ laser was used for excitation at 514 nm. The beam passed through a high-pass dichroic mirror and a notch filter before it reached the sample. The DNA chip was inverted on a clean cover slip on top of a 60× air objective. Fluorescence emission was collected by the same objective and directed through a bandpass filter (585 nm±5 nm, ensuring only fluorescence from rhodamine was observed) to a CCD. In order to track the fluorescence of a certain area, a pattern was scratched on the gold so that exactly the same area could be examined before and after hybridization for comparison. At least four areas at different positions of the gold were chosen for each sample during fluorescence measurement. Under laser illumination, the images were recorded by the CCD camera at 10 s integration time.

Example 4

Hybridization of Targets T1 and T2 to H1- and H2-Functionalized Gold Films

Having prepared the sensor chip containing hairpin probes H1 and H2 bound to the gold surface, hybridization of their respective targets, T1 and T2, was performed at room temperature for 16 hours under the same buffer conditions (e.g., in 0.5 M NaCl buffer containing 20 mM Cacodylic acid, 0.5 mM EDTA, 0.5 M NaCl, pH=7). The 16-hour incubation time was chosen primarily for convenience; preliminary experiments with the hybridization of T1 to H1 suggest that shorter incubation times are possible (see Table 3 below).

TABLE 3

Affect of Hybridization Time on Fluorescent Detection

| Hybridization Time (in minutes): | 10 | 20 | 30 | 60 | 120 | 240 | 360 |
|---|---|---|---|---|---|---|---|
| Fluorescence increase (fold) | 4.1 | 5.8 | 6.1 | 9.0 | 12.2 | 11.1 | 10.5 |

Figure 12A:
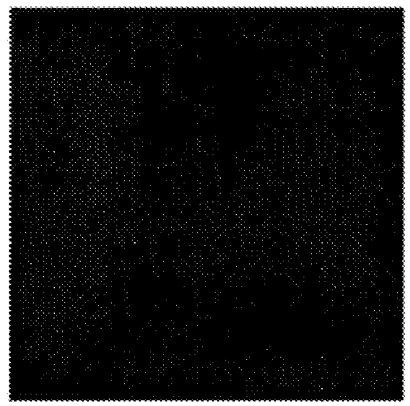
Figure 12B:
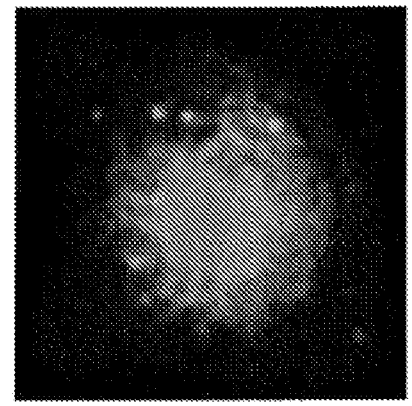
Figure 13A:
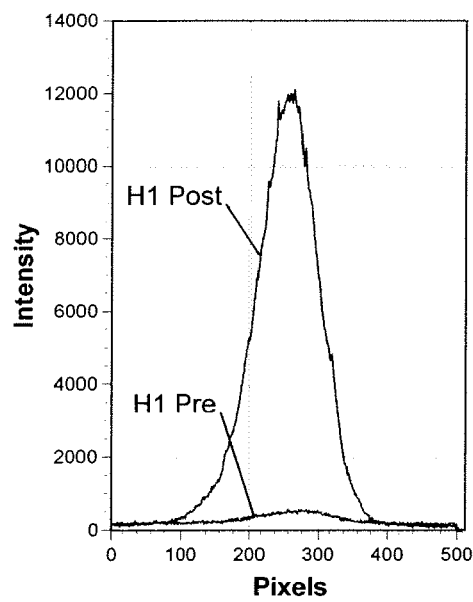
FIGS. 13A-B are graphs illustrating the hybridization-dependent fluorescence efficiency of the sensors containing nucleotide sequences H1 (FIG. 13A) and H2 (FIG. 13B). The fluorescence efficiency was determined using CCD images with dark counts subtracted and all pixels binned in the vertical direction, for both sequences before and after hybridization. The integration time was 10 seconds.
Figure 13B:
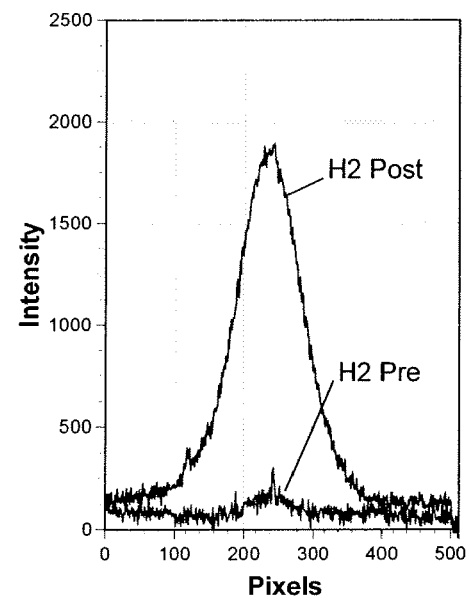

Using epi-fluorescence confocal microscopy, the fluorescence of H1 and H2-functionalized gold films was examined in the presence and absence of T1 and T2, respectively (compare FIGS. 12A and 13A with FIGS. 12B and 13B). As noted above in Example 3, films were excited at 514 nm. Strong reflected laser scatter was removed using the dichroic beamsplitter and a laser-line notch filter. Sample emission was collected by a CCD attached to an imaging spectrograph and passed through a band-pass filter (585 nm±5 nm) to ensure that only rhodamine fluorescence was being observed.

Fluorescence quenching of the hairpins prior to addition of T1 or T2 was calculated as follows:

$$Q = 100 \times \{1 - (I_{probe} - I_{blank})/(I_{target} - I_{blank})\}$$

where:

$I_{probe}$ The fluorescence intensity of hairpin probe on gold before hybridization $I_{target}$ The fluorescence intensity of hairpin probe on gold after hybridization with the target sequences $I_{blank}$ The fluorescence intensity of background including bare gold, cover slip and buffer.

The fluorescence quenching by the gold surface was found to be 96±3% for H1 (FIG. 13A) and 95±4% for H2 (FIG. 13B). This is similar to quenching efficiencies obtained in solution-phase assays (Dubertret et al., *Nature Biotech.* 19:365-370 (2001), which is hereby incorporated by reference in its entirety). Viewed another way, this corresponds to a 26-fold fluorescence enhancement for H1 in the presence of 1.38 μM T1, or 20-fold enhancement in the presence of 2.29 μM T2. Preliminary experiments designed to test the sensitivity of this technique indicated that this system could detect complementary DNA concentrations as low as 10 nM. However, this is by no means an optimized value. Based on the oligonucleotide coverage on Au surfaces (Demers et al., *G. Anal Chem.* 72:5535-5541 (2000), which is hereby incorporated by reference in its entirety), it is expected that optimization of the probe, site size, site density, and instrument design will improve detection to the fM level. It has also been observed that fluorescence unquenching of the chip is reversible, as washing the hybridized ("on") surface with unbuffered water restores it to a quenched ("off") state. Cycles of hybridization/washing results in a monotonic decrease in fluorescence intensity, presumably due to loss of probe hairpin from the Au surface.

Figure 14A:
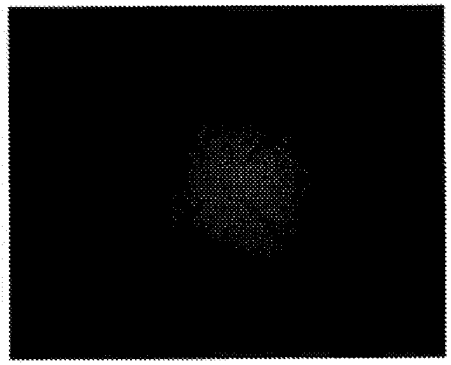
FIGS. 14A-D illustrate the selectivity of hybridization assays.
Figure 14B:
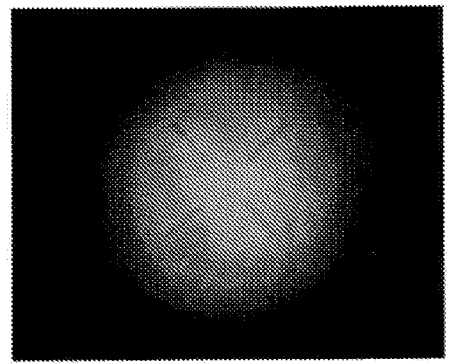
Figure 14C:
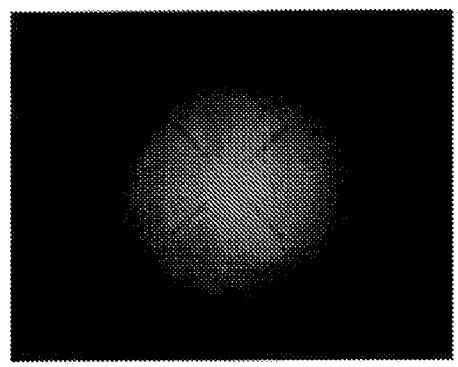

As shown in FIG. 14A-C, sensitivity was limited by a small background signal at 585 nm. This signal had a similar spectrum to that arising from just a pure Au film or a quartz coverslip, indicating that it was due to autofluorescence from the optical system.

Figure 14D:
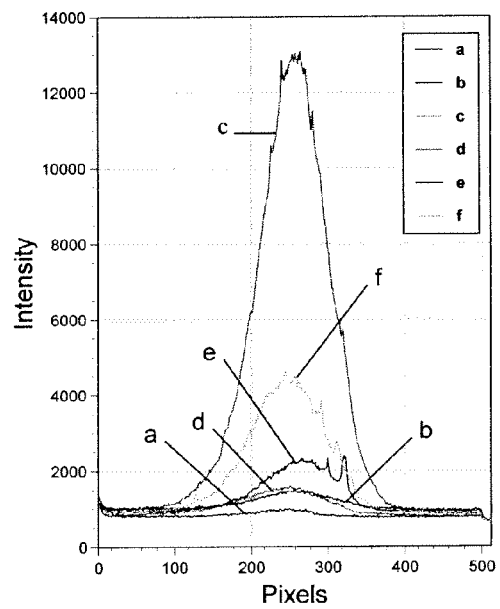

Binding specificity (sequence selectivity) is obviously a significant measure of the utility of a diagnostic device or biosensor. To evaluate the extent to which the Au-immobilized probes retained their hybridization selectivity, the ability of equivalent concentrations of T1 and salmon sperm DNA (USB Corporation) to produce a signal when incubated with a H1-functionalized gold substrate were compared. As shown in FIG. 14D, an approximately 26-fold increase in intensity (over background) was measured for the sample corresponding to the appropriate complementary DNA (curve c). In contrast, an equivalent concentration of salmon sperm DNA produces only a 4-fold increase of fluorescence intensity (curve f). This result indicates that DNA hairpins immobilized on a gold surface retain their ability to bind complementary DNA sequences selectively. That the salmon sperm DNA produces a net increase in intensity is not surprising, as a standard BLAST database search (Altschul et al., *Nucl. Acids Res.* 25:3389-3402 (1997), which is hereby incorporated by reference in its entirety) of the sequences T1 and T2 indicates that sequences homologous to portions of these are present in a variety of organisms.

While under laser illumination, the fluorescence intensity was observed to irreversibly decay with time, likely due to photobleaching of the dye molecule. For an excitation intensity of 600 W/cm², the signal intensity was reduced by a factor of 2 in a second. However, the rate of decay was linearly proportional to the excitation intensity for intensities in the range 6 to 600 W/cm². Thus, to avoid any ambiguities caused by the permanent photobleaching, all measurements were taken at intensities less than 20 W/cm². This is a lower intensity than is commonly employed by commercial microarray scanners; however, direct comparisons are difficult given the differences in scan times.

The above results demonstrate that fluorophore-tagged DNA hairpins attached to gold films can function as highly sensitive and selective sensors for oligonucleotides. For two distinct DNA hairpin sequences, binding by the complement caused an increase in signal by over a factor of 20, while non-specific sequences resulted in a minimal response.

Example 5

Detecting of Mismatches Using Hairpin-Immobilized on Gold Film

Figure 15A:
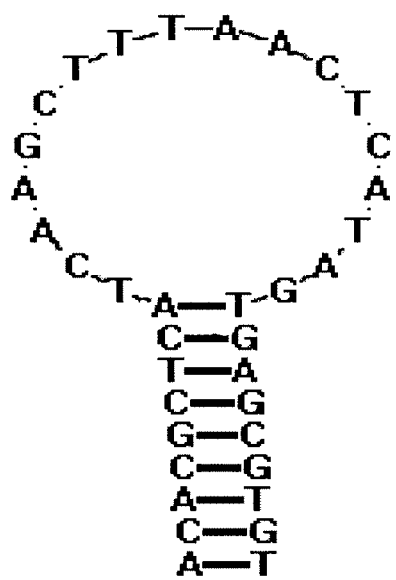
FIGS. 15A-C illustrate the secondary structure of hairpin H3 alone (15A), and the hybrids H3-T3 (15B) and H3-T3M1 (15C). H3 was derived from probe H1, described in FIG. 5. Each of H3, T3, and T3M1 were ordered from Midland Certified Reagent Co. (Midland, Tex.). The folding structure was predicted using the computer program RNAStructure version 3.7 (Mathews et al., *J. Mol. Biol.* 288:911-940 (1999), which is hereby incorporated by reference in its entirety).

A hairpin H3 (FIG. 15A) was prepared by modification of hairpin H1. In particular, nucleotides 13-24 of H1 (SEQ ID NO: 1) were removed, forming H3 shown in Table 4 below. Similarly, target T3 was prepared by modification of target T1, specifically by removing nucleotides 25-37 from T1 (SEQ ID NO: 11), forming T3 shown in Table 4 below. Mismatch target T3M1 was prepared by modifying nt 6 of T3 (from C→G), as shown in Table 4 below.

TABLE 4

Sequences used in Example 5

| Entry | SEQ ID NO: | Sequence |
|---|---|---|
| H3 | 13 | (C6Thiol)-acacgctcatcaagctttaactcatagtgag cgtgt-Rhodamine |
| T3 | 14 | acgctcactatgagttaaagcttg |
| T3M1 | 15 | acgctgactatgagttaaagcttg |

Figure 15B:
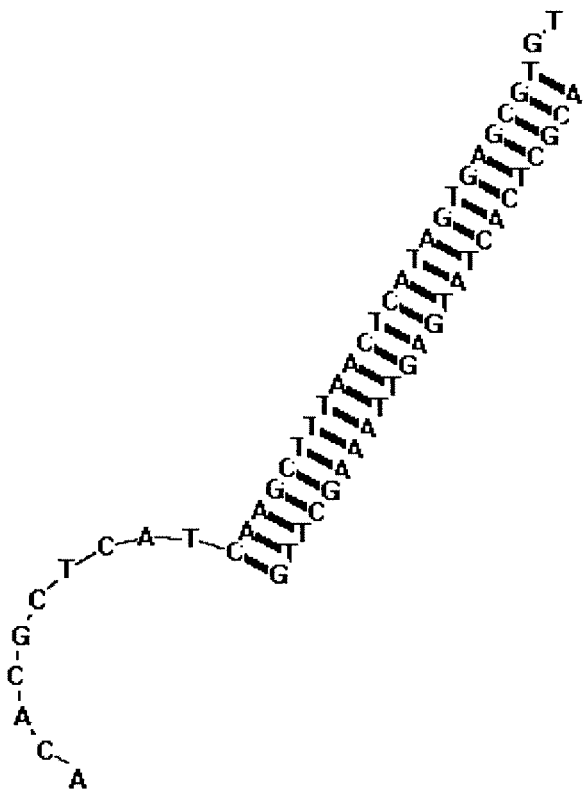
Figure 15C:
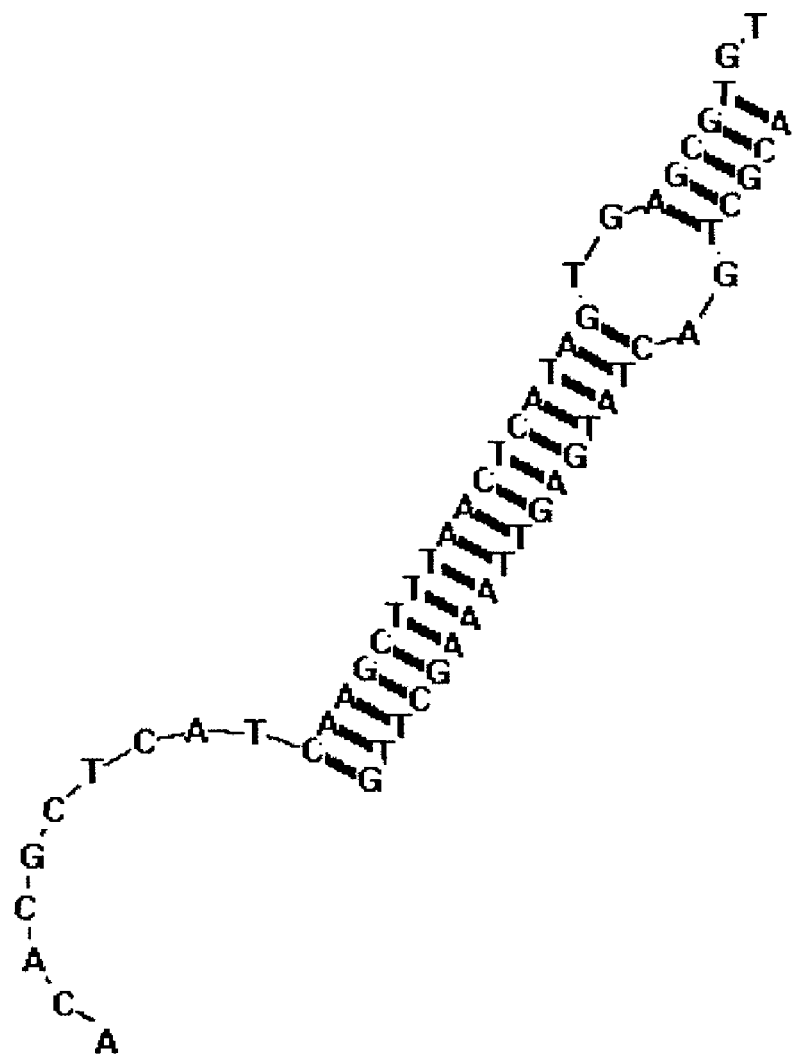

H3 and its respective complementary strands T3 (FIG. 15B) and T3M1 (containing a single mismatch, FIG. 15C) were obtained from a commercial supplier (Invitrogen Corporation, Carlsbad, Calif.). H3 was bound to a gold surface in the same manner as described in Example 2 above.

Figure 16A:
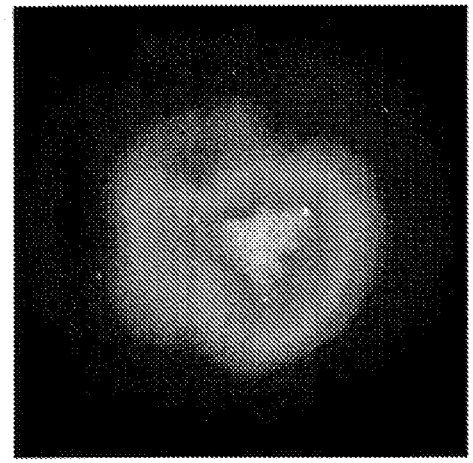
FIGS. 16A-C illustrate the effects of a single-base mismatch on the stability of the hybrids and the ability of the mismatch to maintain disruption of the hairpin formation (i.e., promoting fluorescence). CCD images illustrate the readily apparent differences in fluorescent intensity (compare FIGS. 16A-B). The graph presented in FIG. 16C represents the binned CCD images, which reflect a nearly five-fold reduction in fluorescence intensity for the target possessing a single mismatch.
Figure 16B:
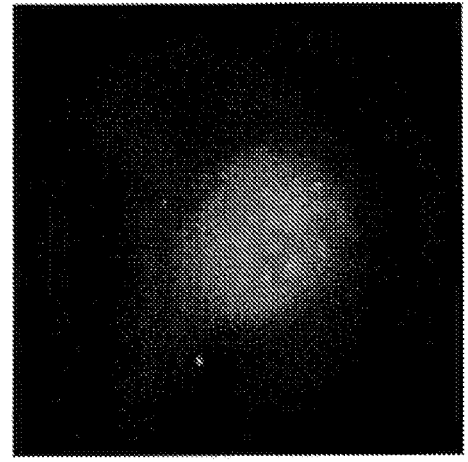
Figure 16C:
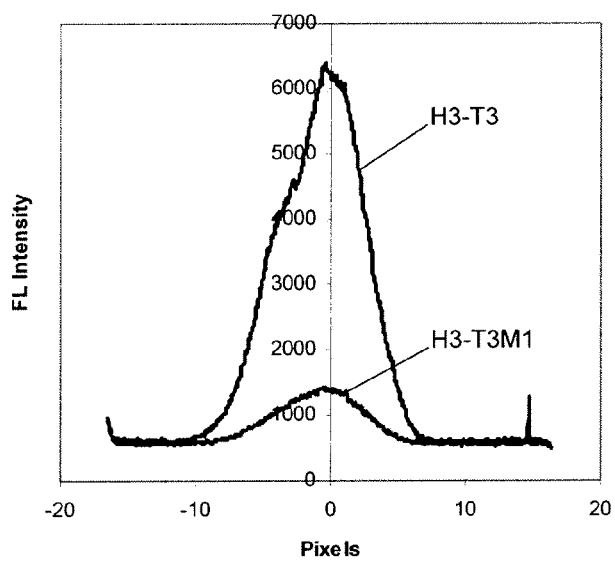

Hybridization between H3 bound to the gold surface and either T3 or T3M1 was performed under the same conditions described in Example 3 above. The CCD images obtained illustrate the readily apparent differences in fluorescent intensity (compare FIGS. 16A-B) caused by the single base mismatch. The graph presented in FIG. 16C represents the binned CCD images, which reflect a nearly five-fold reduction in fluorescence intensity (efficiency) for the target possessing a single mismatch. This example indicates that the present invention can readily be used to discriminate between a target nucleic acid having perfectly matched bases a nucleic acids possessing polymorphisms, such as single-nucleotide polymorphisms ("SNPs"). Therefore, the present invention is expected to be useful for purposes of analyzing genomic information for the presence of SNPs and other polymorphisms.

Example 6

Preparation of DNA Hairpins Targeted to *Bacillus anthracis* DNA

Two DNA hairpins, HP1 and HP2 (Table 5 below), were designed to incorporate portions of the *Bacillus anthracis* partial pag gene, isolate IT-Carb3-6254 (Genbank Accession AJ413936, which is hereby incorporated by reference in its entirety). These hairpins were designed according to the procedures described in co-pending U.S. Provisional Patent Application Ser. No. 60/533,894 to Miller et al., filed Jan. 2, 2004, now U.S. patent application Ser. No. 10/584,875 (as a national stage application of PCT/US2005/000053, filed Jan. 3, 2005), which is expressly incorporated by reference in its entirety.

TABLE 5

Sequences used in Example 7

| Entry | SEQ ID NO: | Sequence |
|---|---|---|
| HP1 | 6 | (C6Thiol)-tttctttcaccatggatttctaatattcatg aaaagaaa-Rhodamine |
| HP2 | 5 | (C6Thiol)-tcgttagtgttaggaaaaaatcaaacactcg cga-Rhodamine |
| TP1 | 16 | tttcttttcatgaatattagaaatccatggtgaaagaaa |
| TP2 | 17 | tcgcgagtgtttgatttttcctaacactaacga |

Basically, a partial gene sequence of the above-identified pag gene was obtained from the Genbank database and the secondary structure of an approximately 1000 nucleotide region was predicted using computer program RNAStructure version 3.7 (Mathews et al., *J. Mol. Biol.* 288:911-940 (1999), which is hereby incorporated by reference in its entirety). From this predicted structure, two naturally occurring hairpins were identified. One appeared at nt 668-706 of the pag sequence from Genbank Accession AJ413936. The other appeared at nts 1209-1241 of the pag sequence from Genbank Accession AJ413936.

Having identified these two sequences, these sequences were isolated from the larger sequence and subjected to a second structure prediction as above. The predicted structure of HP1 is characterized by a predicted free energy value of about −4.4 kcal/mol. The predicted structure of HP2 is characterized by a predicted free energy value of about −4.7 kcal/mol. In addition, these two hairpins are each within the size range of about 30-40 nucleotides. Having selected HP1 and HP2, a final structural prediction of the duplexes (HP1-TP1 and HP2-TP2) was carried out to determine the predicted free energy value for the duplexes. The duplex HP1-TP1 was predicted to have a free energy value of −43.2 kcal/mol and the duplex HP2-TP2 was predicted to have a free energy value of −42.6 kcal/mol. These values indicate that the hybridization between the hairpin and the target will be an energetically favorable process. A BLAST search was independently performed using the HP1 and HP2 sequences, the results indicating that only pag genes from other *Bacillus anthracis* isolates contain highly related nucleotide sequences.

Example 7

Preparation and Testing of Sensor Chips Targeted to *Bacillus anthracis* DNA (C6-thiol)-HP1-Rhodamine and (C6-thiol)-HP2-Rhodamine, as well as their respective complementary strands TP1 and TP2 (FIGS. 17A-B and FIG. 18A-B), were obtained from a commercial supplier. A sensor chip for identifying *Bacillus anthracis* DNA, specifically DNA for the pag gene, was prepared by immobilizing HP1 and HP2 onto a gold-coated substrate in accordance with Example 2 above.

Figure 18A:
FIGS. 18A-C illustrate the hybridization-dependent fluorescence efficiency of a sensor chip containing hairpin probe HP2.
Figure 18B:
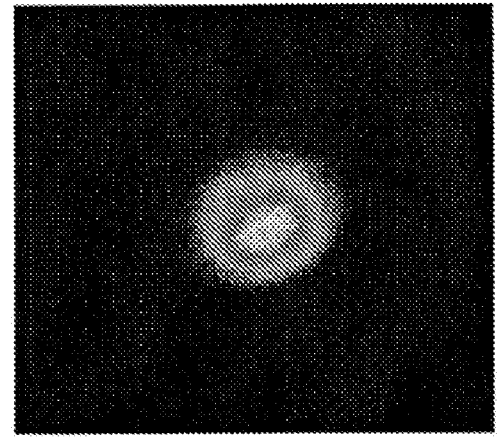
Figure 18C:
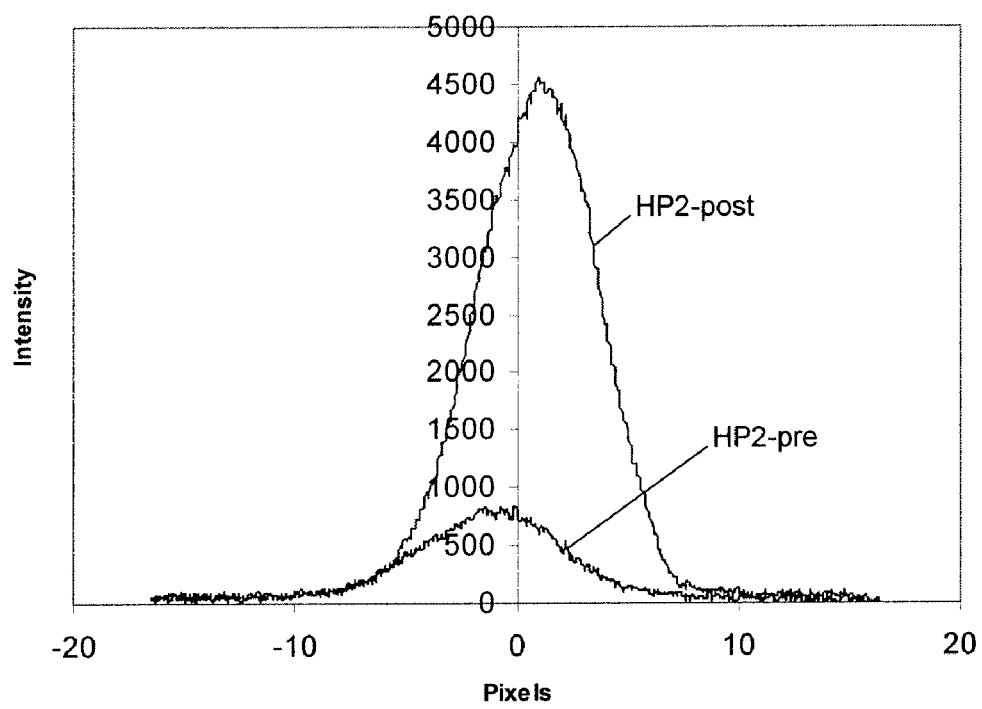

Hybridization between HP1 bound to the gold surface and TP1, as well as HP2 bound to the gold surface and TP2, was performed under the same conditions described above in Example 3 above. The CCD images obtained illustrate the readily apparent differences in fluorescent intensity for HP1-TP1 hybridization (compare FIGS. 17A-B) and for HP2-TP2 hybridization (compare FIGS. 18A-B). The graph presented in FIG. 17C represents the binned CCD images, which illustrate a nearly 24-fold increase in fluorescence intensity upon target binding. Likewise, the graph present in FIG. 18C represents the binned CCD images, which illustrate a nearly six-fold increase in fluorescence intensity upon target binding.

Together, these data indicate that the present invention can readily be used to prepare hairpin sensors capable of identifying the presence of target DNA in a sample. Although T3 was a synthetic nucleic acid representative of *Bacillus anthracis* pag gene, it is expect that the DNA from samples containing *Bacillus anthracis* should produce similar results given the specificity of the selected hairpin.

Example 8

Preparation of DNA Hairpins Targeted to *Staphylococcus aureus* DNA

Two DNA hairpins, AH2 and BH2 (Table 6 below), were designed to incorporate portions of the *Staphylococcus aureus* genome (Genbank Accession AP003131, which is hereby incorporated by reference in its entirety). These hairpins were designed according to the procedures described in co-pending U.S. Provisional Patent Application Ser. No. 60/533,894 to Miller et al., filed Jan. 2, 2004, now U.S. patent application Ser. No. 10/584,875 (as a national stage application of PCT/US2005/000053, filed Jan. 3, 2005), which is expressly incorporated by reference in its entirety.

TABLE 6

Sequences used in Example 9

| Entry | SEQ ID NO: | Sequence |
|---|---|---|
| AH2 | 9 | (C6Thiol)-cgataatatgatgcctaggcagaaatattatcg-Rhodamine |
| BH2 | 10 | (C6Thiol)-tatcaataataaacgaatagggtgttaatattgata-CY5 |

TABLE 6-continued

Sequences used in Example 9

| Entry | SEQ ID NO: | Sequence |
|---|---|---|
| AH2-C | 18 | cgataatatttctgcctaggcatcatattatcg |
| BH2-C | 19 | tatcaatattaacacccctattcgtttattattgata |

Basically, a segment of the complete *Staphylococcus aureus* genome was obtained from the Genbank database and the secondary structure of the obtained segment was predicted using computer program RNAStructure version 3.7 (Mathews et al., *J. Mol. Biol.* 288:911-940 (1999), which is hereby incorporated by reference in its entirety). From this predicted structure, two naturally occurring hairpins were identified, one corresponding to AH2 and the other corresponding to BH2.

Having identified these two sequences, these sequences were isolated from the larger sequence and subjected to a second structure prediction as above. The predicted structure of AH2 is characterized by a predicted free energy value of about −6.1 kcal/mol (FIG. 23). The predicted structure of BH2 is characterized by a predicted free energy value of about −3.5 kcal/mol (FIG. 24). In addition, these two hairpins are each within the size range of about 30-40 nucleotides. Having selected AH2 and BH2, a final structural prediction of the duplexes (AH2-AH2C and BH2-BH2C) was carried out to determine the predicted free energy value for the duplexes. The duplex AH2-AH2C was predicted to have a free energy value of −38.3 kcal/mol and the duplex BH2-BH2C was predicted to have a free energy value of −39.0 kcal/mol. These values indicate that the hybridization between the hairpin and the target will be an energetically favorable process. A BLAST search was independently performed using the AH2 and BH2 sequences, the results indicating that only segments of the *Staphylococcus aureus* genome contain highly related nucleotide sequences.

Example 9

Preparation of Single Chips Containing Two Hairpins that Identify Distinct Targets (C6-thiol)-AH2-Rhodamine and its complementary strand AH2-C was obtained from Midland Certified Reagent Co. (Midland, Tex.). (C6-thiol)-BH2-CY5 and its complementary strands BH2-C was obtained from Integrated DNA Technologies, Inc. (Carlsbad, Calif.).

Glass slides were cleaned with piranha etch solution (4:1 concentrated $H_2SO_4$/30% $H_2O_2$) overnight at room temperature, and then rinsed with Nanopure water. Metal deposition was performed at a rate of 0.2 nm/s using Denton Vacuum Evaporator (DV-502A). First, a chromium adhesion layer of 7 nm was coated on the glass, followed by 100 nm thick gold films. Before use, the gold substrates were annealed at 200° C. for 4 hour and cleaned with piranha solution for 0.5-1 hr.

Two sensor chips for identifying *Staphylococcus aureus* DNA were prepared by immobilizing AH2-Rhodamine and BH2-CY5 onto the same gold-coated substrate. AH2-Rhodamine and BH2-CY5 were mixed together in 1:1 ratio. The gold substrate was soaked in a mixture solution of hairpin oligonucleotide and mercaptopropanol at a ratio of 1 to 10 for self-assembly. Two hours later, the substrate was thoroughly rinsed with hot water (90° C. or higher) to get rid of the non-bonded DNA and then was immersed in 0.5 M NaCl buffer (20 mM Cacodylic acid, 0.5 mM EDTA, 0.5 M NaCl, pH=7) for 1-2 hours. Next, two substrates carrying the mixed probes were incubated in the target solutions for AH2 and BH2, respectively, for hybridization at room temperature for 16 hours under the same buffer conditions.

Fluorescence measurement was performed on a Nikon inverted fluorescence microscope equipped with a liquid nitrogen cooled CCD. A CW laser (Millenia, Spectra-Physics) was used for excitation at 532 nm. The beam passed through a high-pass dichroic mirror and a notch filter before it reached the sample. The DNA chip was inverted on a clean cover slip on top of a 60× air objective. Fluorescence emission was collected by the same objective and directed through a long pass filter (570 nm) to a CCD. To track the fluorescence of a certain area, a pattern was scratched on the gold so that exactly the same area could be examined before and after hybridization for comparison. At least four areas at different positions of the gold were chosen for each sample during fluorescence measurement. Under laser illumination, the images were recorded by the CCD camera at 5 s integration time and the spectra were recorded at 30 s integration time. For each spot, images were taken, first at a spectrum 550 nm to 630 nm (for rhodamine) and then at 620 nm to 700 nm (for CY5).

Figure 19A:
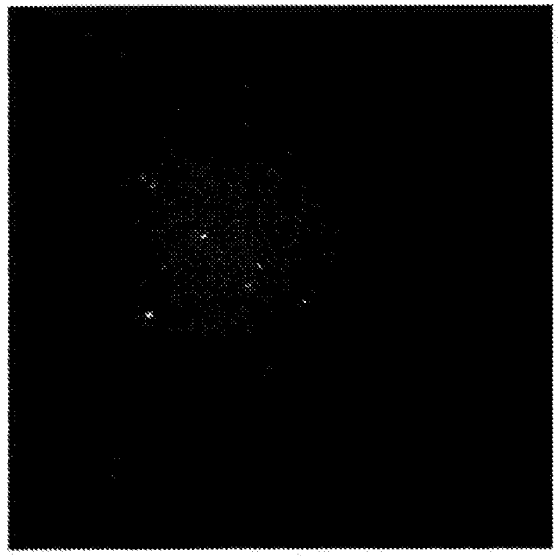
FIGS. 19A-D illustrate the CCD images obtain pre- and post-hybridization for two chips, AB-3 and AB-4, both of which were prepared with hairpin probe overlay using two distinct hairpins that target different nucleic acids and have different fluorescent signals. One probe, designated AH2-Rhodamine, contains the fluorophore rhodamine, which produces peak emissions at around 585 nm; whereas the other probe, designated BH2-Cy5, contains the fluorophore Cy5, which produces peak emissions at around 670 nm. Thus, fluorescent emissions by the two probes can be discriminated spectrally. Chip AB-3 was incubated with 3.0 μM of hybridizing target AH2C (the complement to probe AH2), and chip AB-4 was incubated with 3.0 μM of hybridizing target BH2C (the complement to probe BH2).
Figure 19B:
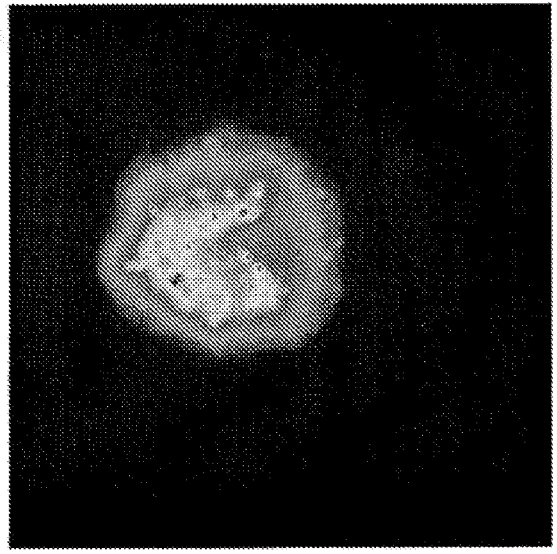
Figure 19C:
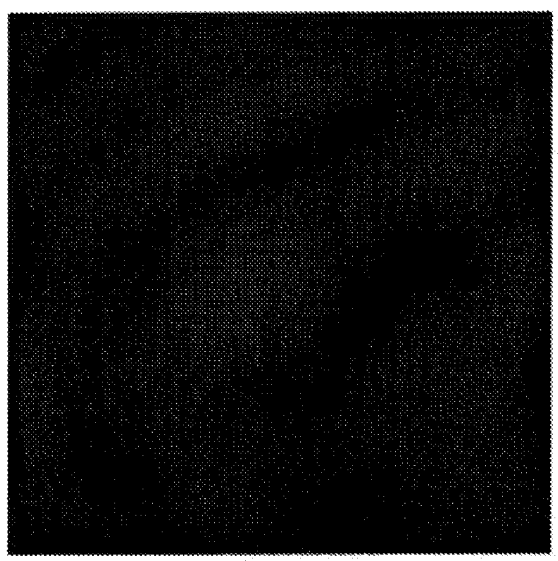
Figure 19D:
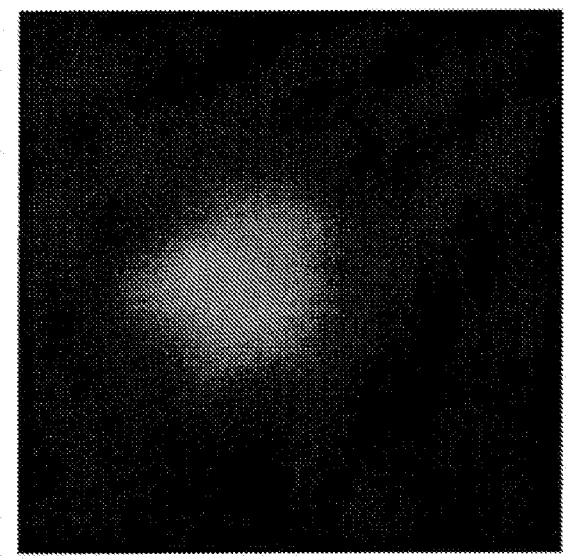
Figure 20A:
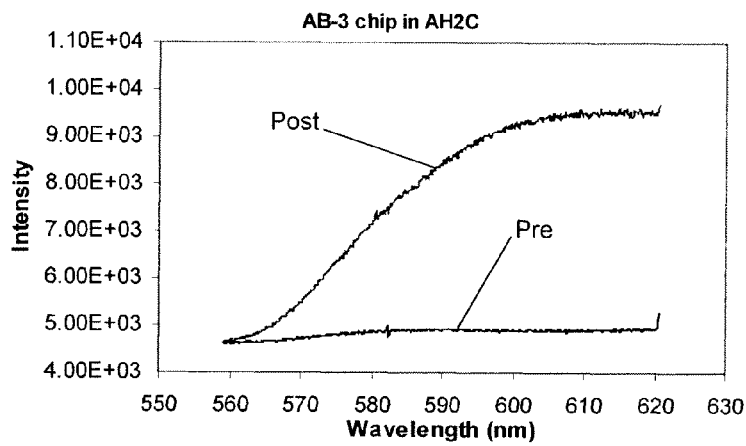
FIGS. 20A-F are binned images and fluorescent spectra showing the results of exposing chips AB-3 and AB-4 to the hybridizing targets AH2C and BH2C.
Figure 20B:
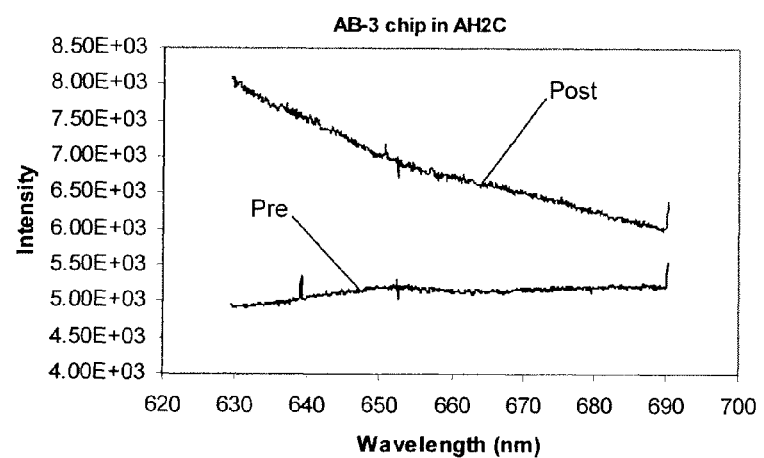
Figure 20C:
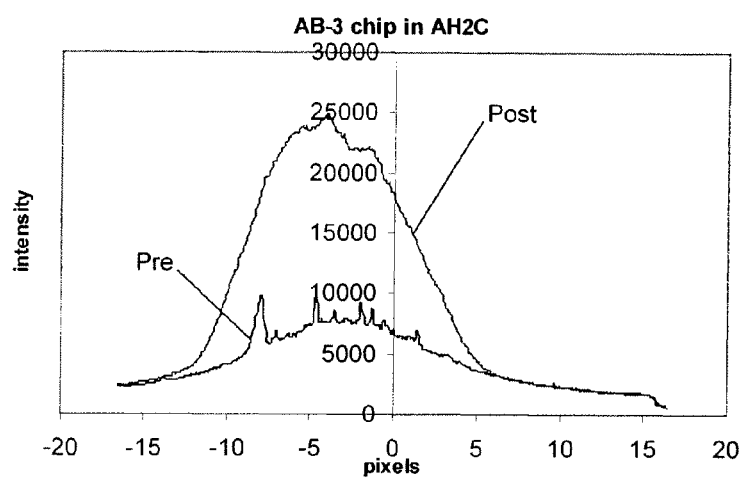
Figure 20D:
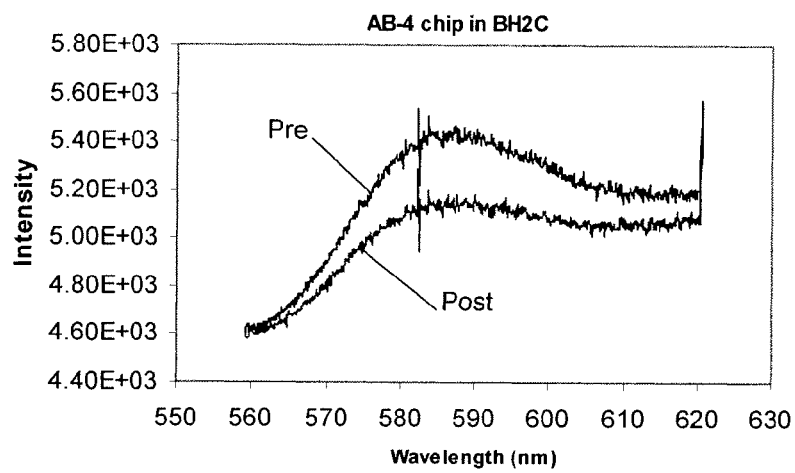
Figure 20E:
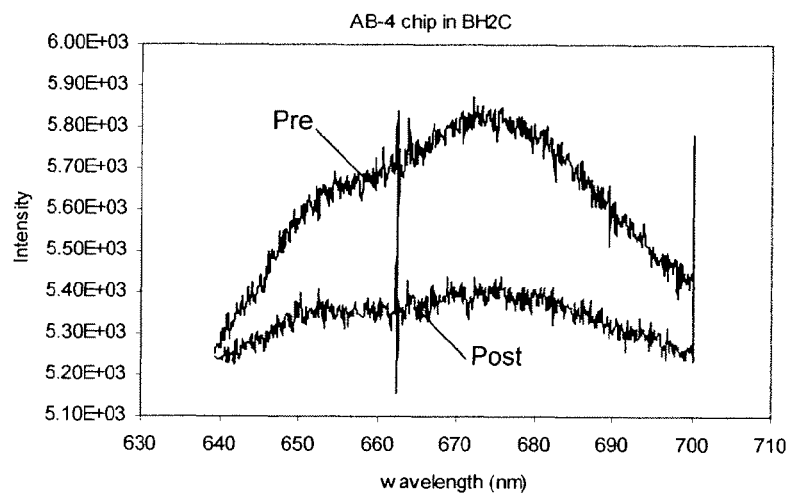
Figure 20F:
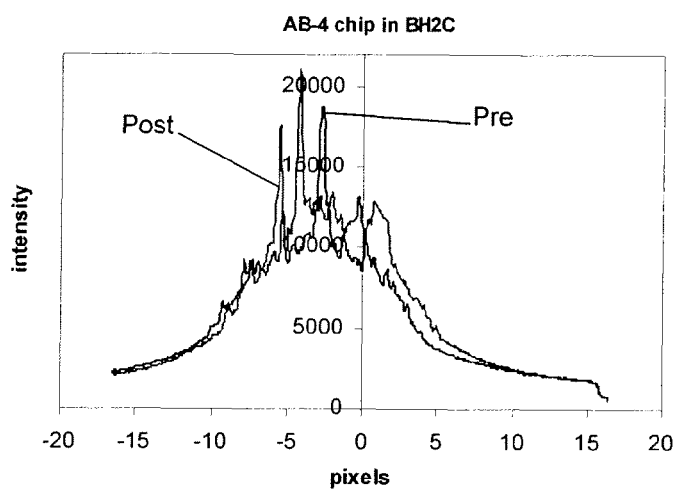

For chip AB-3, the increase of Rhodamine is higher than that of Cy5, so the fluorescence increase of the chip is mainly due to probe AH2-AH2C hybridization, rather than BH2-AH2C hybridization (FIGS. 19A-B; FIGS. 20A-B). The increase in fluorescence emission for chip AB-3 is about 3.6-fold (FIG. 20C). For chip AB-4, the increase of Cy5 is higher than that of Rhodamine, so the fluorescence increase of the chip is mainly due to probe BH2-BH2C hybridization, rather than AH2-BH2C hybridization (FIGS. 19C-D; FIGS. 20D-E). The increase in fluorescence emission for chip AB-4 is about 1.6 fold (FIG. 20F).

Example 10

Preparation of Hairpin Probe Labeled with Cdse Nanocrystal as Fluorophore

CdSe nanocrystals capped with ZnS were dissolved in hexane as stock solution. Two ml of the nanocrystal stock solution was washed with methanol three times. The washed nanocrystals were then introduced into 0.5 ml N,N-dimethylformamide (DMF), followed by adding 12 µL dihydrolipoic acid (DHLA). The reaction was allowed to proceed overnight under nitrogen and in dark. Thereafter, the nanocrystals were precipitated and washed twice with acetonitrile. About 1.79 mg 1-ethyl-3-(3-dimethylaminopropyl) carbodiimide hydrochloride (EDC) was added to the nanocrystal-acetonitrile solution. After about four hours, the nanocrystals were washed again with acetonitrile. An aqueous solution of oligonucleotide hairpins (having the 3' end modified with an amine group) was mixed with nanocrystals under mild stirring and at room temperature. About 24 hours later, the labeled oligonucleotide hairpins were washed in methanol and then dissolved in water or mild saline buffer solution for subsequent use.

It is expected that the nanocrystal-labeled hairpin will afford orders of magnitude more photostability for the sensor chips as compared to the dye-labeled hairpins described in the preceding examples.

Example 11

Preparation of DNA Hairpins Targeted to Methicillin-Resistant *Staphylococcus*

*Staphylococcus areus* gene sequence mecR was obtained electronically from the National Center for Biotechnological Information (NCBI). The genomic sequences were subsequently divided into 600 nucleotide sequences in the following pattern: 1-600, 301-900, 601-1200, et cetera. Breaking the larger sequences into smaller portions greatly reduced the computational strain produced when the predicted structures of the segments were analyzed and also increased the ease with which the output was analyzed. The predicted secondary structures of the smaller sub-sections of the sequence were then analyzed using the folding algorithm contained in the program RNAStructure v3.7 (Mathews et al., *J. Mol. Biol.* 288:911-940 (1999), which is hereby incorporated by reference in its entirety). Portions of the predicted structures that were produced are shown in FIG. 27. Regions of the folded structures that exhibited the highest degree of "hairpin-like" structure were then analyzed independently using RNAStructure v4.2 (Mathews et al., *Proc. Natl. Acad. Sci.* 101:7287-7792 (2004), which is hereby incorporated by reference in its entirety) to verify that the structural integrity was a product of the sequence, and not an artifact of the overall large structure. The level of "hairpin-like" structure was determined by visual inspection, looking for probes that were ~30-40 nucleotides in length and had 50-70% of their nucleotides in a Watson-Crick base pair. Structures that were deemed to be suitably stable as hairpins were then analyzed in their duplexed form using RNAStructure v4.2 to ensure that the hybridization would be thermodynamically favorable.

TABLE 7

Sequences used in Example 11

| Entry | SEQ NO: | Sequence |
|---|---|---|
| mecR sense | 20 | caggttaatttgaaaaatatgaaacaacataa catg |
| mecR antisense | 21 | (C6Thiol)-catgttatgttgtttcatattt ttcaacaaattaacctg-3'(Amino C7) (TMR) |

The secondary structures of the complementary sequences formed two dimensional mirror images of the original structures and possessed favorable free energies of formation that were either very similar or identical to the originals. The predicted structure of SEQ ID NO: 20 is characterized by a predicted free energy value of about −4.2 kcal/mol (FIG. 25). The predicted structure of SEQ ID NO: 21 is characterized by a predicted free energy value of about −3.7 kcal/mol (FIG. 26). The corresponding duplex is characterized by a predicted free energy value of about −43.3 kcal/mol. While the complementary sequences for other hairpin have all been predicted to form stable secondary structures, the predicted structures have not always been mirror images of the original hairpin.

The probe sequences of SEQ ID NOS: 20 and 21 are distinguishable from the H2 probe sequence listed in Table 1 (and its target), because—unlike H2—substantially the entire sequence of SEQ ID NOS: 20 and 21 are designed to hybridize to the target. A comparison of H2 and T2 shows that about 9 bases at the 3' end of H2 were added to the probe to form the hairpin. Thus, over the length of H2, only about 77 percent of the bases are designed to hybridize to the target, whereas for SEQ ID NOS 20 and 21, 100 percent of the bases are designed to hybridize to the target.

To check the specificity for the intended targets, a BLAST search was performed on the antisense probe sequences. The search results for the mecR probe produced hits for three different species of Staphylococci (*S. aureus, S. sciuri*, and *S. epidermis*). A "hit" was defined as a sequence that was fully complementary to the probe sequence, because—as shown in Example 5—anything other than a perfect match is readily distinguished with surface immobilized molecular beacons of the present invention. This confirms that mecR chromosomal DNA is not unique to *S. aureus* alone, but it is unique to methicillin-resistant strains of *Staphylococcus* spp.

The beacons illustrated in Table 7 above were immobilized using the procedures described in Example 9 above. Target DNA was introduced to the chip using the following conditions: 2.5 µM synthetic target DNA in 0.5 M NaCl, 20 mM cacodylic acid, and 0.5 mM EDTA, and hybridization at 22° C.

The rate at which the targeted DNA was able to hybridize to the surface immobilized probe was determined by monitoring the signal that was produced over time in response to introduction of the target. The results of these studies are shown in FIG. 28, which illustrates detectable probe illumination within minutes. Measurements taken at 5 minutes were greater than 60% of the final signal output, and near peak fluorescence was achieved within about 30 minutes.

The ability of surface immobilized molecular beacons to detect the presence of their target DNA sequences in a solution of inhomogeneous DNA is critical. To test this capability, total RNA was extracted and purified from methicillin-resistant *Staphylococcus areus* cultures. RNA extraction using the modified acid phenol/chloroform technique yielded an average of 800-1000 µg of RNA. The average A260/A280 was between 1.85 and 2.0, indicating that the product was pure oligonucleotide. Aliquots of total RNA were diluted to 230 µg/mL in NaCl buffer (0.5 M NaCl, 20 mM cacodylic acid, 0.5 mM EDTA) and were then spiked with solutions of the synthetic complement for the mecR probe such that the final concentrations of synthetic targets were 100 nM and 1 nM. Individual gold films were functionalized with the mecR probe, as described above, and were then submerged into the mixed solutions and allowed to incubate at room temperature (22° C.).

FIG. 29 shows representations of the fluorescent intensities produced by the surface immobilized molecular beacons both before and after treatment with the samples spiked with the synthetic complement for the mecR probe. Despite the presence of an excess of non-specific oligonucleotide, the mecR immobilized films produced strong signals in response to the presence of the synthetic target. Importantly, subjecting surface immobilized mecR chips to total RNA purified from *E. coli* JM109 without the additional presence of synthetic target DNA produced no observable increase in signal.

Example 12

Demonstration of mecR Functionality in an Arrayed Format 10-15 µm spots of a 2 µM mecR/10 µM mercaptopropanol solution were arrayed onto a gold surface. After one hour, the surface was washed and hairpin reformation was facilitated by treatment with 0.5 M NaCl buffer. Images of the 200×600 µm area containing the arrays, taken before and after treatment with a 2.5 µM target solution, are shown in FIG. 30.

Example 13

Preparation of DNA Hairpins Targeted to *Staphylococcus aureus*

The procedure used to identify the hairpins targeted to *Staphylococcus aureus* is the same as detailed above in Example 11.

The predicted secondary structures of the smaller subsections of the sequence were then analyzed using the folding algorithm contained in the program RNAStructure v3.7 (Mathews et al., *J. Mol. Biol.* 288: 911-940 (1999), which is hereby incorporated by reference in its entirety). Regions of the folded structures that exhibited the highest degree of "hairpin-like" structure were then analyzed independently using RNAStructure v4.2 (Mathews et al., *Proc. Natl. Acad. Sci.* 101:7287-7792 (2004), which is hereby incorporated by reference in its entirety) to verify that the structural integrity was a product of the sequence, and not an artifact of the overall large structure. The level of "hairpin-like" structure was determined by visual inspection, looking for probes that were ~30-40 nucleotides in length and had 50-70% of their nucleotides in a Watson-Crick base pair. Structures that were deemed to be suitably stable as hairpins were then analyzed in their duplexed form using RNAStructure v4.2 to ensure that the hybridization would be thermodynamically favorable.

TABLE 8

Sequences used in Example 13

| Entry | SEQ NO: | Sequence |
| --- | --- | --- |
| *Staphylococcus aureus* genome (sense) | 22 | gataatatgatgcctaggcagaaatattatc |
| *Staphylococcus aureus* genome (antisense) | 23 | gataatatttctgcctaggcatcatattatc |
| *Staphylococcus aureus* genome (sense) | 24 | atatcaataataaacgaataggggtgttaatattgatat |
| *Staphylococcus aureus* genome (antisense) | 25 | atatcaatattaacacccctattcgtttattattgatat |
| *Staphylococcus aureus* genome (sense) | 26 | gtgatgtattagaaagaaatttataataaatcac |
| *Staphylococcus aureus* genome (antisense) | 27 | gtgatttattataaatttctaatacatcac |

The secondary structures of the complementary sequences formed two dimensional mirror images of the original structures and possessed favorable free energies of formation that were either very similar or identical to the originals.

The predicted structure of SEQ ID NO: 22 is illustrated in FIG. 31, and is characterized by a predicted free energy value of about −3.9 kcal/mol. The predicted structure of SEQ ID NO: 23 is illustrated in FIG. 32, and is characterized by a predicted free energy value of about −3.3 kcal/mol. The corresponding duplex is characterized by a predicted free energy value of about −33.9 kcal/mol.

The predicted structure of SEQ ID NO: 24 is illustrated in FIG. 33, and is characterized by a predicted free energy of −4.4 kcal/mol. The predicted structure of SEQ ID NO: 25 is illustrated FIG. 34, and is also characterized by a predicted free energy of −3.7 kcal/mol. The corresponding duplex is characterized by a predicted free energy value of about −40.8 kcal/mol.

The predicted structure of SEQ ID NO: 26 is illustrated in FIG. 35, and is characterized by a predicted free energy of −9.9 kcal/mol. The predicted structure of SEQ ID NO: 27 is illustrated FIG. 36, and is characterized by a predicted free energy of −4.0 kcal/mol. The corresponding duplex is characterized by a predicted free energy value of about −33.9 kcal/mol.

To check the specificity for the intended targets, a BLAST search was performed on the antisense probe sequences. A "hit" was defined as a sequence that was fully complementary to the probe sequence, because—as shown in Example 5—anything other than a perfect match is readily distinguished with surface immobilized molecular beacons of the present invention. For each of the probes listed in Table 8, BLAST results show 100% specificity for *Staphylococcus aureus*.

Example 14

Preparation of DNA Hairpins Targeted to *Staphylococcus epidermidis* rpoB Gene

The procedure used to identify the hairpins targeted to *Staphylococcus epidermidis* is the same as detailed above in Example 11.

The predicted secondary structures of the smaller subsections of the sequence were then analyzed using the folding algorithm contained in the program RNAStructure v3.7 (Mathews et al., *J. Mol. Biol.* 288:911-940 (1999), which is hereby incorporated by reference in its entirety). Regions of the folded structures that exhibited the highest degree of "hairpin-like" structure were then analyzed independently using RNAStructure v4.2 (Mathews et al., *Proc. Natl. Acad. Sci.* 101:7287-7792 (2004), which is hereby incorporated by reference in its entirety) to verify that the structural integrity was a product of the sequence, and not an artifact of the overall large structure. The level of "hairpin-like" structure was determined by visual inspection, looking for probes that were ~30-40 nucleotides in length and had 50-70% of their nucleotides in a Watson-Crick base pair. Structures that were deemed to be suitably stable as hairpins were then analyzed in their duplexed form using RNAStructure v4.2 to ensure that the hybridization would be thermodynamically favorable.

TABLE 9

Sequences used in Example 14

| Entry | SEQ NO: | Sequence |
|---|---|---|
| *Staphylococcus epidermidis* rpoB 147 sense | 28 | gcagagttaacgcacaaacgtcgtttatctgc |
| *Staphylococcus epidermidis* rpoB 147 antisense | 29 | gcagataaacgacgtttgtgcgttaactctgc |
| *Staphylococcus epidermidis* rpoB 205 sense | 30 | aacgtgctcaaatggaagtgcgtgacgtt |
| *Staphylococcus epidermidis* rpoB 205 antisense | 31 | aacgtcacgcacttccatttgagcacgtt |

The predicted structure of SEQ ID NO: 28 is characterized by a predicted free energy value of about −6.8 kcal/mol (FIG. 37). The predicted structure of SEQ ID NO: 29 is characterized by a predicted free energy value of about −8.2 kcal/mol (FIG. 38). The corresponding duplex is characterized by a predicted free energy value of about −42.5 kcal/mol.

The predicted structure of SEQ ID NO: 30 is illustrated by FIG. 39 and is characterized by a predicted free energy of about −3.9 kcal/mol (FIG. 39). The predicted structure of SEQ ID NO: 31 is characterized by a predicted free energy value of about −2.1 kcal/mol (FIG. 40). The corresponding duplex is characterized by a predicted free energy value of about −40.2 kcal/mol.

To check the specificity for the intended targets, a BLAST search was performed on the antisense probe sequences. The search results for the rpoB 147 antisense probe (table 9) produced hits only for *S. epidermidis*, indicating that these probes are specific for this species. The search results for the rpoB 205 antisense probe (table 9) produced hits for nine species of *Staphylococcus*, indicating that this probe is not useful for discriminating among *Staphylococcus* spp. The rpoB 147 sense and antisense probes, when used in combination with the mecR probes of SEQ ID NOS: 20 and/or 21, can be used to discriminate *S. epidermidis* from *S. aureus* and *S. sciuri*.

Example 15

Preparation of DNA Hairpins Targeted to *Staphylococcus sciuri* DnaJ Gene

The procedure used to identify the hairpins targeted to *Staphylococcus sciuri* is the same as detailed above in example 11.

The predicted secondary structures of the smaller subsections of the sequence were then analyzed using the folding algorithm contained in the program RNAStructure v3.7 (Mathews et al., *J. Mol. Biol.* 288:911-940 (1999), which is hereby incorporated by reference in its entirety). Regions of the folded structures that exhibited the highest degree of "hairpin-like" structure were then analyzed independently using RNAStructure v4.2 (Mathews et al., *Proc. Natl. Acad. Sci.* 101:7287-7792 (2004), which is hereby incorporated by reference in its entirety) to verify that the structural integrity was a product of the sequence, and not an artifact of the overall large structure. The level of "hairpin-like" structure was determined by visual inspection, looking for probes that were ~30-40 nucleotides in length and had 50-70% of their nucleotides in a Watson-Crick base pair. Structures that were deemed to be suitably stable as hairpins were then analyzed in their duplexed form using RNAStructure v4.2 to ensure that the hybridization would be thermodynamically favorable.

TABLE 10

Sequences used in Example 15

| Entry | SEQ NO: | Sequence |
|---|---|---|
| *Staphylococcus sciuri* DnaJ 465 sense | 32 | cttgtacgtactgtaacggacaag |
| *Staphylococcus sciuri* DnaJ 465 antisense | 33 | cttgtccgttacagtacgtacaag |
| *Staphylococcus sciuri* DnaJ 546 sense | 34 | gtcctgaatgtgaaggttctggac |

TABLE 10-continued

Sequences used in Example 15

| Entry | SEQ NO: | Sequence |
|---|---|---|
| Staphylococcus sciuri DnaJ 546 antisense | 35 | gtccagaaccttcacattcaggac |
| Staphylococcus sciuri DnaJ 681 sense | 36 | tagctggtaaaggtggtccaggta |

The predicted structure of SEQ ID NO: 32 is characterized by a predicted free energy value of about −5.3 kcal/mol (FIG. 41). The predicted structure of SEQ ID NO: 33 is characterized by a predicted free energy value of about −2.9 kcal/mol (FIG. 42). The corresponding duplex is characterized by a predicted free energy value of about −29.5 kcal/mol.

The predicted structure of SEQ ID NO: 34 is illustrated in FIG. 43 and is characterized by a predicted free energy of about −3.3 kcal/mol (FIG. 43). The predicted structure of SEQ ID NO: 35 is characterized by a predicted free energy value of about −2.3 kcal/mol (FIG. 44). The corresponding duplex is characterized by a predicted free energy value of about −30.3 kcal/mol.

The predicted structure of SEQ ID NO: 36 is illustrated in FIG. 45 and is characterized by a predicted free energy of about −2.9 kcal/mol (FIG. 45). The complementary probe is predicted not to form a stable hairpin structure (predicted free energy value of about −1.8 kcal/mol), and its predicted structure is therefore not shown. Nevertheless, the corresponding duplex is characterized by a predicted free energy value of about −30.6 kcal/mol.

To check the specificity for the intended targets, a BLAST search was performed on the antisense probe sequences. The search results for the DnaJ 465 and DnaJ 681 antisense probes resulted in hits only for *Staphylococci sciuri*. These probes, when used in combination with the mecR probes of SEQ ID NOS: 20 and/or 21, can be used to discriminate *S. sciuri* from *S. aureus* and *S. epidermidis*. The DnaJ 546 antisense probe was not specific, producing hits from several other *Staphylococcus* spp.

In addition to the foregoing examples, it should be appreciated that additional design considerations can be implemented. For example, sensitivity of the sensor chip can be further optimized through surface enhancement provided by roughened quenching (e.g., metal) substrates (Cao et al., *Science* 297:1536-1540 (2002); Haes et al., *J. Am. Chem. Soc.* 124:10596-10604 (2002), each of which is hereby incorporated by reference in its entirety). Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An isolated nucleic acid molecule that is less than about 60 nucleotides in length, is characterized by being able to self-anneal into a hairpin conformation, and hybridizes to a target nucleic acid that is unique to methicillin-resistant *Staphylococcus* spp. such that said isolated nucleic acid molecule includes not more than two nucleotides that do not hybridize to the target nucleic acid over the length of said isolated nucleic acid molecule.

2. The isolated nucleic acid molecule according to claim 1 further comprising a fluorophore tethered to one end thereof.

3. The isolated nucleic acid molecule according to claim 2 wherein the fluorophore is a dye, a protein, or a semiconductor nanocrystal.

4. The isolated nucleic acid molecule according to claim 1 wherein one end comprises a C6 thiol-modified base.

5. The isolated nucleic acid molecule according to claim 1 wherein the isolated nucleic acid molecule comprises the nucleotide sequence of SEQ ID NO: 20 or SEQ ID NO: 21.

6. The isolated nucleic acid molecule according to claim 5, wherein the isolated nucleic acid molecule consists of SEQ ID NO: 20 or SEQ ID NO: 21.

7. A sensor chip comprising:
a fluorescence quenching surface;
a first nucleic acid molecule according to claim 1 having first and second ends, and being tethered at the first end to the fluorescence quenching surface; and
a first fluorophore bound to the second end of the first nucleic molecule;
whereby when the first nucleic acid molecule is in the hairpin conformation, the fluorescence quenching surface substantially quenches fluorescent emissions by the first fluorophore, and when the first nucleic acid molecule is in a non-hairpin conformation fluorescent emissions by the fluorophore are substantially free of quenching by the fluorescence quenching surface.

8. The sensor chip according to claim 7 further comprising:
a second nucleic acid molecule that is different from the first nucleic acid molecule and specifically binds to nucleic acids from only one species of methicillin-resistant *Staphylococcus*, has first and second ends with the first end bound to the fluorescence quenching surface, and is characterized by being able to self-anneal into a hairpin conformation; and
a second fluorophore bound to the second end of the second nucleic acid molecule;
whereby when the second nucleic acid molecule is in the hairpin conformation, the fluorescence quenching surface substantially quenches fluorescent emissions by the second fluorophore, and when the second nucleic acid molecule is in a non-hairpin conformation, fluorescent emissions by the second fluorophore are substantially free of quenching by the fluorescence quenching surface.

9. The sensor chip according to claim 8 wherein the first nucleic acid molecule comprises one or both of SEQ ID NO: 20 and SEQ ID NO: 21, and wherein the second nucleic acid molecule comprises:
one or more of the nucleotide sequences of SEQ ID NO: 22, SEQ ID NO: 23, SEQ ID NO: 24, SEQ ID NO: 25, SEQ ID NO: 26, and SEQ ID NO: 27;
one or more of the nucleotide sequences of SEQ ID NO: 28, SEQ ID NO: 29, SEQ ID NO: 30, and SEQ ID NO: 31; and
one or more of the nucleotide sequences of SEQ ID NO: 32, SEQ ID NO: 33, SEQ ID NO: 34, SEQ ID NO: 35, and SEQ ID NO: 36.

10. The sensor chip according to claim 8 wherein the second nucleic acid molecule consists of the nucleotide sequence of SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 32, SEQ ID NO: 33, or SEQ ID NO: 36.

11. The sensor chip according to claim 8 wherein the second nucleic acid molecule is capable of distinguishing *S. aureus* from other methicillin-resistant *Staphylococcus*.

12. The sensor chip according to claim 8 wherein the second nucleic acid molecule is capable of distinguishing *S. sciuri* from other methicillin-resistant *Staphylococcus*.

13. The sensor chip according to claim 8 wherein the second nucleic acid molecule is capable of distinguishing *S. epidermidis* from other methicillin-resistant *Staphylococcus*.

14. The sensor chip according to claim 8, wherein the first and second nucleic acid molecules are present in the form of an array.

15. A biological sensor device comprising:
a sensor chip according to claim 7;
a light source that illuminates the sensor chip at a wavelength suitable to induce fluorescent emissions by the first fluorophore; and
a detector positioned to detect fluorescent emissions by the first fluorophore.

16. A method of detecting the presence of a target nucleic acid molecule in a sample comprising:
exposing the sensor chip according to claim 7 to a sample under conditions effective to allow any target nucleic acid molecule in the sample to hybridize to the first nucleic acid molecule, causing the first nucleic acid molecule into the non-hairpin conformation;
illuminating the sensor chip with light sufficient to cause emission of fluorescence by the first fluorophore; and
determining whether or not the sensor chip emits fluorescent emissions of the first fluorophore upon said illuminating, wherein fluorescent emission by the sensor chip indicates that the first nucleic acid molecule is in the non-hairpin conformation and therefore that the target nucleic acid molecule is present in the sample.

17. A method of detecting the presence of a methicillin-resistant strain of *Staphylococcus* in a sample comprising:
providing the sensor chip according to claim 7, wherein the first nucleic acid molecule hybridizes specifically to a target nucleic acid molecule from a methicillin-resistant strain of *Staphylococcus*;
exposing the sensor to a sample under conditions effective to allow any target nucleic acid molecule in the sample to hybridize to the first nucleic acid molecule, causing the first nucleic acid molecule into the non-hairpin conformation;
illuminating the sensor chip with light sufficient to cause emission of fluorescence by the first fluorophore; and
determining whether or not the sensor chip emits fluorescent emissions of the first fluorophore upon said illuminating, wherein fluorescent emission by the sensor chip indicates that the first nucleic acid molecule is in the non-hairpin conformation and therefore that the target nucleic acid molecule is present in the sample, thereby identifying presence of the methicillin-resistant strain of *Staphylococcus* in the sample as tested.

18. An isolated nucleic acid molecule that is less than about 60 nucleotides in length, is characterized by being able to self-anneal into a hairpin conformation, and comprises the nucleotide sequence of SEQ ID NO: 20, SEQ ID NO: 21, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, or SEQ ID NO: 36.

19. A sensor chip comprising:
- a fluorescence quenching surface;
- two or more nucleic acid probe molecules each having first and second ends, being characterized by the ability to self-anneal into a hairpin conformation, and being tethered at the first end to the fluorescence quenching surface, wherein the two or more nucleic acid molecules comprise different nucleotide sequences selected from the group consisting of SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, and SEQ ID NO: 36; and
- a fluorophore bound to the second end of each nucleic molecule;
- whereby when nucleic acid probe molecules are in the hairpin conformation, the fluorescence quenching surface substantially quenches fluorescent emissions by the first fluorophore, and when the nucleic acid molecules are in a non-hairpin conformation fluorescent emissions by the fluorophore are substantially free of quenching by the fluorescence quenching surface.

20. The sensor chip according to claim 19, wherein the two or more nucleic acid probe molecules are present in the form of an array.

21. A biological sensor device comprising:
- a sensor chip according to claim 19;
- a light source that illuminates the sensor chip at a wavelength suitable to induce fluorescent emissions by the fluorophore; and
- a detector positioned to detect fluorescent emissions by the fluorophore.

22. A method of detecting the presence of a target nucleic acid molecule in a sample comprising:
- exposing the sensor chip according to claim 19 to a sample under conditions effective to allow any target nucleic acid molecule in the sample to hybridize to its corresponding nucleic acid probe molecules, causing the nucleic acid probe molecule to adopt the non-hairpin conformation;
- illuminating the sensor chip with light sufficient to cause emission of fluorescence by the fluorophores; and
- determining whether or not the sensor chip emits fluorescent emissions of the fluorophores upon said illuminating, wherein fluorescent emission by the fluorophore of one nucleic acid probe molecule indicates that the target nucleic acid molecule for the one probe molecule is present in the sample.

23. An isolated nucleic acid molecule that consists of SEQ ID NO: 22 or SEQ ID NO: 23.

* * * * *